United States Patent [19]

Simmons

[11] Patent Number: 5,656,603

[45] Date of Patent: Aug. 12, 1997

[54] AMINOPEPTIDASE P INHIBITORS AND USES THEREOF

[75] Inventor: William H. Simmons, LaGrange Park, Ill.

[73] Assignee: Loyola University of Chicago, Chicago, Ill.

[21] Appl. No.: 455,281

[22] Filed: May 31, 1995

[51] Int. Cl.$^6$ .............. A61K 38/06; C07K 5/00; C07K 7/00; C07K 16/00

[52] U.S. Cl. .............. 514/17; 514/19; 514/18; 530/328; 530/329; 530/330; 530/332; 562/567

[58] Field of Search .............. 530/331–328, 530/329, 330, 332; 562/567; 514/17–19

[56] References Cited

FOREIGN PATENT DOCUMENTS 04178398  6/1992  Japan .............. C07K 5/08

OTHER PUBLICATIONS

Ahmad, et al., "Depressor Action of Bradykinin Agonists Relative to Metabolism by Angiotensin–Converting Enzyme, Carboxypeptidase N, and Aminopeptidase P", P.S.E.B.M., 200: 115–121 (1992).

Allemann, et al., "Insulin Sensitivity In Normotensive Subjects During Angiotensin Converting Enzyme Inhibition With Fosinopril", Eur. J. Clin. Pharmacol 42: 275–280 (1992).

Ambrosioni, et al., "The Effect of the Angiotensin–Converting–Enzyme Inhibitor Zofenopril on Mortality And Morbidity After Anterior Myocardial Infarction," The New England Journal of Medicine, 332: 80–85 (Jan. 12, 1995).

Auch-Schwelk, et al., "Local Potentiation of Bradykinin–Induced Vasodilation by Converting–Enzyme Inhibition in Isolated Coronary Arteries," Journal of Cardiovascular Pharmacology, 20 (Suppl. 9): S62–S67 (1992).

Baker, Jr., et al., "Kinin Metabolism in the Perfused Ventilated Rat Lung. 1: Bradykinin Metabolism in a System Modeling The Normal, Uninjured Lung," Circulatory Shock 33: 37–47 (1991).

Baker, Jr., et al., "Kinin Metabolism in the Perfused Ventilated Rat Lung. II: Influence of Ventilation, Perfusion, and Perfusate Composition Variation on Bradykinin Metabolism in Uninjured Lung," Circulatory Shock 37: 280–290 (1992).

Bao, et al., "Chronic Kinin Receptor Blockade Attenuates the Antihypertensive Effect of Ramipril," Hypertension 20: 74–79 (1992).

Bao et al., "Role of Bradykinin in Chronic Antihypertensive Actions of Ramipril in Different Hypertension Models," Journal of Cardiovascular Pharmacology 20 (Suppl. 9): S96–S99 (1992).

Baumgarten, et al., "Ramiprilat Increases Bradykinin Outflow From Isolated Hearts of Rat," Br. J. Pharmacol. 108: 293–295 (1993).

Bhoola, et al., "Bioregulation of Kinins: Kallikreins, Kininogens, and Kininases" Pharmacological Review 44: 1–80 (1992).

Bonner, et al. "Hemodynamic Effects of Bradykinin on Systemic and Pulmonary Circulation in Healthy and Hypertensive Humans," Journal of Cardiovascular Pharmacology 15 (Suppl. 6) S46–S56 (1990).

Bonner, G., "Kinin–Related Effects of Angiotensin–Converting Enzyme Inhibition," Clinical Physiology and Biochemistry 9: 6–15 (1990).

Burley, et al., "Structure Determination and Refinement of Bovine Lens Leucine Aminopeptidase and its Complex with Bestatin," J. Mol. Biol. 224: 113–140 (1992).

Cachofeiro, et al., "Kinins, Nitric Oxide, and the Hypotensive Effect of Captopril and Ramiprilat in Hypertension," Hypertension 19: 138–145 (1992).

Carbonnell, et al., "Effect of a Kinin Antagonist on the Acute Antihypertensive Activity of Enalaprilat in Severe Hypertension," Hypertension 11: 239–243 (1988).

Carretero, et al., "Kinins as Regulators of Blood Flow and Blood Pressure," Hypertension: Pathophysiology, Diagnosis and Management, 805–817 (1990).

Castro, et al., "B.O.P.: A New Peptide Coupling Reagent Exemplified in the Synthesis of Somatostatin," in Peptides 1976 )Loffet, A., ed.) pp. 79–84, Univ. of Brussels (1976).

Cornish-Bowden, A., "A Simple Graphical Method for Determining the Inhibition Constants of Mixed, Uncompetitive and Non–Competitive Inhibitors," Biochem. J. 137: 143–144 (1974).

(List continued on next page.)

Primary Examiner—Cecilia J. Tsang
Assistant Examiner—M. Borin
Attorney, Agent, or Firm—Marshall, O'Toole, Gerstein, Murray & Borun

[57] ABSTRACT

The present invention is directed to a compound of the formula:

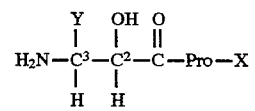

or a pharmaceutically acceptable addition salt thereof, wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid having a radius of gyration of less than 1.54 Å, X also having a carboxyl or a carboxyamide moiety at its carboxy terminus. The present invention is further directed to a pharmaceutical composition and to a method of inhibiting bradykinin degradation in a patient using the above-described compound.

32 Claims, 7 Drawing Sheets

OTHER PUBLICATIONS

Dehm, et al., "The Cleavage of Prolyl Peptides by Kidney Peptidases," Eur. J. Biochem. 17: 364–371 (1970).

Dixon, M., "The Determination of Enzyme Inhibitor Constants," Biochem. J. 55: 170–171 (1953).

Dorer, et al., "Hydrolysis of Bradykinin by Angiotensin-Converting Enzyme," Cir. Res. 34: 824–827 (1974).

Dos Santos Medeiros, et al. "Processing and Metabolism of Peptide-YY: Pivotal Roles of Dipeptidylpeptidase-IV, Aminopeptidase-P, and Endopeptidase-24.11," Endocrinology 134: 2088–2094 (1994).

Farhy, et al., "Kinins Mediate The Antiproliferative Effect Of Ramipril In Rat Carotid Artery," Biochemical and Biophysical Research Communications, 182: 283–288 (1992).

Farhy, et al., "Role of Kinins and Nitric Oxide in the Effects of Angiotensin Converting Enzyme Inhibitors on Neointima Formation," Circulation Research 72: 1202–1210 (Jun. 1993).

Lasch, et al., FEBS Letters, "Enzymic Properties Of Intestinal Aminopeptidase P: A New Continuous Assay," 227: 171–174 (Jan., 1988).

Fleminger, et al., "Fluorogenic Substrates for Bacterial Aminopeptidase P And Its Analogs Detected In Human Serum and Calf Lung," Euro. J. Biochem 125: 609–615 (1982).

Gavras, H., "Angiotensin-Converting Enzyme Inhibition and the Heart," Hypertension 23: 813–818 (Jun. 1994).

Harada, et al., "High-performance Liquid Chromatographic Determination of Aminopeptidase P Activity in Fischer F344 Rat Serum and Kidney," Journal of Chromatography, 493: 176–181 (1989).

Harbeck, et al., "Aminopeptidase P From Rat Brain," Eur. J. Biochem. 198: 451–458 (1991).

Hartman, eta l., "Reduction of Myocardical Infarct Size in Rabbits by Ramiprilat: Reversal by the Bradykinin Antagonist HOE 140," J. Cardiovasc. Pharmacol. 21: 996–1003 (1993).

Hartman, et al., "Reduction of Myocardial Infarct Size by Ramiprilat Is Independent of Angiotensin II Synthesis Inhibition," European Journal of Pharmacology, 234: 229–236 (1993).

Hecker, et al., "Relaxation of Isolated Coronary Arteries by Angiotensin-converting Enzyme Inhibitors: Role of Endothelium-Derived Kinins," J. Vas. Res. 30: 257–262 (1993).

Hecker, et al., "Potentiation by ACE Inhibitors Of The Dilator Response To Bradykinin In The Coronary Microcirculation: Interaction At the Receptor Level," Br. J. Pharmcol. 111: 238–244 (1994).

Heller, et al., "The Effect of Kinin and Prostaglandin Inhibitors On The Renal Response To Angiotensin-Converting Enzyme Inhibition: A Micropuncture Study In The Dog," Pflügers Arch. 427: 219–224 (1994).

Hendriks, et al., "Aminopeptidase P And Dipeptidyl Peptidase IV Activity In Human Leukocytes And In Stimulated Lymphocytes," Clinica Chimica Acta. 196: 87–96 (1991).

Hooper, et al., "Purification and Characterization of Pig Kidney Aminopeptidase P," Biochem. J. 267: 509–515 (1990).

Hooper, et al., "Inhibition by Converting Enzyme Inhibitors of Pig Kidney Aminopeptidase P," Hypertension 19: 281–285 (1992).

Hooper, et al., "Ectoenzymes of the Kidney Microvillar Membrane," FEBS Letters 229: 340–344 (1988).

Ishida, et al., "Role of Angiotensin Converting Enzyme and Other Peptidases in In Vivo Metabolism of Kinins," Hypertension 14: 322–327 (1989).

Johnson, et al., "Neutral Metalloendopeptidase in Human Lung Tissue and Cultured Cells," Am. Rev. Respir. Dis. 132, 564–568 (1985).

Segel, I.H., Enzyme Kinetics, John Wiley and Sons, New York, (1975) pp. 64–71.

Kiowski, et al., "Coronary Vasodilatation and Improved Myocardial Lactate Metabolism After Angiotensin Converting Enzyme Inhibition With Cilazapril In Patients With Congestive Heart Failure," American Heart Journal, 1382–1388 (1991).

Kitamura, et al., "Inhibition of Aminopeptidase P Potentiates The Vassodepressor Response To Bradykinin," Hypertension 24: 396 (1994).

Kitamura, et al., "Potentiation By Aminopeptidase P Of Blood Pressure Response To Bradykinin," British Journal of Pharmacology, 114: 6–7 (1995).

Koelsch, et al., "Release of GPI-Anchored Membrane Aminopeptidase P By Enzymes And Detergents Has Some Peculiarities," Biochimica et Biophysica Acta 1190: 170–172 (1994).

Koida, et al., "Post-proline Cleaving Enzyme," The Journal of Biological Chemistry, 1221: 7593–7599 (1976).

Linder, et al., "ACE Inhibitors For The Treatment Of Myocardial Ischemia?," Cardiovascular Drugs and Therapy, 4: 1375–1384 (1990).

Linz, et al., "Bradykinin Prevents Left Ventricular Hypertrophy In Rats," Journal of Hypertension, 11 (Suppl. 5): S96–S97 (1993).

Linz, et al. "Cardiac Arrhythmias Are Ameliorated By Local Inhibition Of Angiotensin Formation And Bradykinin Degradation With The Converting-Enzyme Inhibitor Ramipril," Cardiovascular Drugs and Therapy, 3: 873–882 (1989).

Linz, et al., "Contribution of Bradykinin To The Cardiovascular Effects Of Ramipril," Journal of Cardiovascular Pharmacology, 22 (Suppl. 9): S1–S8 (1993).

Linz, et al., "Local Inhibition of Bradykinin Degradation in Ischemic Hearts," Journal of Cardiovascular Pharmacology, 15 (Suppl. 6): S99–S109 (1990).

Linz, et al., "Role of Bradykinin In The Cardiac Effects Of Angiotensin-Converting Enzyme Inhibitors," Journal of Cardiovascular Pharmacology, 20 (Suppl. 9): S83–S90 (1992).

Martorana, et al. "Reduction of Infarct Size By Local Angiotensin-Converting Enzyme Inhibition Is Abolished By A Bradykinin Antagonist," European Journal of Pharmacology, 182: 395–396 (1990).

Maruyama, et al., "Aminopeptidase P, Capable of Hydrolyzing Oligoproline, From Bovine Brain," Biosci. Biotech. Biochem. 58: 2107–2108 (1994).

Munch, et al., "Bradykinin Increases Myocardial Contractility: Relation To The Gregg Phenomenon," the American Physiological Society, pp. R1095–R1103 (1991).

Noda, et al., "Role of Locally Formed Angiotensin II and Bradykinin In The Reduction Of Myocardial Infarct Size In Dogs," Cardiovascular Research, 27: 334–340 (1993).

Nolly, et al., "A Local Kallikrein-Kinin System Is Present In Rat Hearts," Hypertension, 23: 919–923 (1994).

Orawski, et al., "Aminopeptidase P From Bovine Lung: Solubilization, Properties, And Potential Role In Bradykinin Degradation," Molecular and Cellular Biochemistry, 75: 123–132 (1987).

Orawski, et al., "Degradation of Bradykinin And Its Metabolites By Rat Brain Synaptic Membranes," Peptides, 10: 1063–1073 (1989).

Orawski, et al., "Dipeptidase Activities In Rat Brain Synaptosomes Can Be Distinguished On The Basis Of Inhibition By Bestatin And Amastatin: Identification Of A Kyotorphin (Tyr–Arg)–Degrading Enzyme," Neurochemical Research, 17: 817–820 (1992).

Orawski, et al., "Metabolism Of Bradykinin By Multiple Coexisting Membrane–Bound Peptidases In Lung: Techniques For Investigating The Role Of Each Peptidase Using Specific Inhibitors," Kinins V, Part B, Abe, et al. Editors, Plenum Publishing Co. (1989).

Pelc, et al., "Mechanism of Coronary Vasodilation Produced By Bradykinin," Circulation, 83: 2048–2056 (1991).

Pesquero, et al., "Bradykinin Metabolism Pathway In The Rat Pulmonary Circulation," J. Hyperten. 10, 1471–1478 (1992).

Pesquero, et al., "Pulmonary Kinin Metabolism And Conversion Of Angiotensin I In Spontaneously Hypertensive Rats," J. Hyperten, 10, 1479–1484 (1992).

Ronco, et al., "Distribution of Enkephalinas (Membrane Metalloendopeptidase, E.C. 3.4.24.11) in rat Organs," Lab. Invest. 58, 210–217 (1988).

Segel, I.H. (1975) Enzyme Kinetics, pp. 170–178, John Wiley and Sons, New York.

Prechel, et al. "Effect of An Aminopeptidase P Inhibitor On Bradykinin Degradation in The Isolated Perfused Rat Lung," The 10th International Conference on Intracellular Protein Catabolism (Tokyo), (Oct. 30–Nov. 5, 1994).

Rett, et al., "Metabolic Effects Of Kinins: Historical and Recent Developments," J. of Cardiovascular Pharmacology, 15 (Suppl. 6): S57–S59 (1990).

Rusu, et al., "Aminopeptidase P from Human Leukocytes," Eur. J. Biochem., 210: 93–100 (1992).

Ryan, "Assay of Peptidase And Protease Enzymnes In Vivo," Biochemical Pharmacology, 32: 2127–2137 (1983).

Ryan, et al. "Purification and Characterization of Guinea Pig Serum Aminoacylproline Hydrolase (Aminopeptidase P)," Biochimica et Biophysica Acta., 1119: 140–147 (1992).

Ryan, et al., "Characterization of Rat Pulmonary Vascular Aminopeptidase P in Vivo: Role In The Inactivation of Bradykinin," J. Pharmacol. Exper. Thera. 269: 941–947 (1994).

Ryan, et al., "A Radioassay For Aminoacylproline Hydrolase (aminopeptidase P) Activity," Biochimica et Biophysica Acta, 1119: 133–139 (1992).

Ryan, et al., "Inactivation of Bradykinin In Rat Lung," Adv. Exp. Med. Biol. 8, 263–271 (1970).

Ryan, "Peptidase Enzymes of the Pulmonary Vascular Surface," Am. J. Physiol. 257: L53–L60 (1989).

Scharpe, et al., "Exopeptidases In Human Platelets: An Indication For Proteolytic Modulation Of Biologically Active Peptides," Clinica Chimica Acta, 195: 125–132 (1990).

Scholkens, et al., "Effects Of The Angiotensin Converting Enzyme Inhibitor, Ramipril, In Isolated Ischaemic Rat Heart Are Abolished By A Bradykinin Antagonist," Journal of Hypertension, 6 (Suppl. 4): S25–S28 (1988).

Seymour, et al., "Potentiation Of The Renal Responses To Bradykinin By Inhibition Of Neutral Endopeptidases 3.4.24.11 and Angiotensin–Converting Enzyme In Anesthetized Dogs," Journal of Pharmacology And Experimental Therapeutics, 269: 263–270 (1994).

Sherman, et al., "Methionine Or Not Methionine At The Beginning Of A Protein," BioEssays, 3: 27–31 (1985).

Shimamoto, et al., "Angiotensin–Converting Enzyme Inhibitors And The Kallikrein–Kinin System," J. Cardiovasc. Pharmacol., 15 (Suppl. 6): S83–S90 (1990).

Sidorowicz, et al., "Cleavage of the $ARG^1-PRO^2$ Bond of Bradykinin By A Human Lung Peptidase: Isolation, Characterization, And Inhibition By Several β–Lactam Antibiotics[1] (41828)," Proceedings of The Society For Experimental Biology and Medicine, 175: 503–509 (1984).

Simmons, et al., "Membrane–Bound Aminopeptidase P From Bovine Lung," The Journal of Biological Chemistry, 267: 4897–4903 (1992).

Szechinski, et al., "A Kininase And A Kinin–Converting Enzyme: Two Distinct Alpha Aminoacyl Peptide Hydrolases From Bovine Lung," Enzyme, 29:21–31 (1983).

Tieku, et al., "Inhibition of Aminopeptidases N, A and W," Biochemical Pharmacol., 44: 1725–1730 (1992).

Tobe, et al., "The Angiotensin Converting Enzyme Inhibitor Perindopril Improves Survival After Experimental Myocardial Infarction In Pigs," Journal of Cardiovascular Pharmacology, 19: 732–740 (1992).

Vanhoof, et al., "Kininase Activity In Human Platelets: Cleavage Of The $Arg^1-Pro^2$ Bond Of Bradykinin By Aminopeptidase P," Biochemical Pharmacology, 44: 479–487 (1992).

Vanhoof, et al., "Localization and Characterization Of Aminopeptidase P In Bovine Adrenal Medulla," Neurochem. Int., 21: 203–208 (1992).

Vanhoof, et al., "Proline–Specific Aminopeptidases: Potential Role In Bradykinin Degradation, Recent Progress on Kinins", pp. 120–127 (1992).

Wall, et al., "Role of Bradykinin in Myocardial Preconditioning," The Journal of Pharmacology and Experimental Therapeutics, 270: 681–689 (1994).

Ward, "Metabolism of Bradykinin and Bradykinin Analogs," Bradykinin Antagonists, Basic and Clinical Research (Burch, R.M., ed.) pp. 147–170, Marcel Dekker, New York (1991).

Schechter, et al., "On The Size Of The Active Site In Proteases I., Papain," Biochemical and Biophysical Research Communications, 27: 157–162 (1967).

Umezawa, et al., "Bestatin, An Inhibitor Of Aminopeptidase B, Produced By Actinomycetes," J. Antibiotics 29: 97–99 (1976).

Yaron, et al., "Proline–Dependent Structural and Bioligical Properties of Peptides And Proteins," Clinical Reviews in Biochemistry and Molecular Biology, 28: 31–81 (1993).

Yaron, "The Role Of Proline In The Proteolytic Regulation Of Biologically Active Peptides," Biopolymers, 26: S215–S222 (1987).

Yoshimoto, et al., "Cloning and Expression Of Aminopeptidase P Gene From Escherichia coli HB101 and Characterization of Expressed Enzyme," J. Biochem. 104: 93–97 (1988).

Yoshimoto, et al., "Substrate Specificity of Aminopeptidase P From Escherichia coli: Comparison with Membrane–Bound Forms From Rat And Bovine Lung," Arch. Biochem. Biophys. 311: 28–34 (1994).

AMINOPEPTIDASE P INHIBITORS AND USES THEREOF

BACKGROUND OF THE INVENTION

1. Field of the Invention

The present invention is directed to a compound that is capable of inhibiting the enzyme, aminopeptidase P, whose natural substrate is bradykinin. The compound of the present invention is useful as a pharmaceutical agent because by inhibiting bradykinin degradation, the compound of the present invention allows bradykinin to exert its beneficial effects on the cardiovascular system (including decreasing blood pressure, dilating the coronary arteries, and providing protective effects on the heart during myocardial ischemia reperfusion injuries), to improve renal function, and to improve glucose tolerance and insulin-sensitivity. The present invention is also directed to a method for inhibiting bradykinin degradation in a mammalian patient.

2. Background of the Invention

Bradykinin (Bk) is a nine-amino acid peptide hormone which has recently been shown to have numerous beneficial effects on the cardiovascular system. These include decreased blood pressure, dilation of coronary arteries leading to increased blood flow to heart muscle, and direct protective effects on the heart during myocardial ischemia-reperfusion injuries. Bradykinin can also enhance renal function and improve glucose tolerance and insulin-sensitivity (2). See references as disclosed at the end of the Detailed Description (1–7). However, Bk is rapidly degraded in vivo. Almost complete inactivation of Bk occurs during a single circulation through the lung by peptidases located on the plasma membrane of vascular endothelial cells (8–10). One of the enzymes responsible for inactivation is angiotensin converting enzyme (ACE) (11).

Aminopeptidase P is known to cleave the N-terminal amino acid from peptides that have a prolyl residue in the second position (12, 14, 19). It has been suggested that membrane-bound aminopeptidase P may also have an important role in vivo in the pulmonary degradation of Bk (10–18) by cleaving its $Arg^1$-$Pro^2$ bond. It has also been suggested that other peptidases may also play a role in Bk degradation (13). To date, studies to determine the role of aminopeptidase P in Bk metabolism in vivo have been hampered by the lack of a potent and specific inhibitor of aminopeptidase P. Accordingly, it is an object of the present invention to determine which enzymes, other than ACE, are involved in Bk degradation. It is a further object of this invention to discover and provide an inhibitor of aminopeptidase P. It is also an object of the present invention to provide a method for inhibiting bradykinin degradation in vivo.

SUMMARY OF THE INVENTION

It was discovered that the degradation of the nonapeptide hormone, Bk, by aminopeptidase P is capable of being inhibited by a compound of the formula:

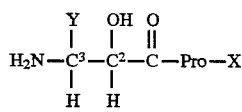

or a pharmaceutically acceptable addition salt thereof,
wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid having a radius of gyration of less than 1.54 Å, X optionally having a carboxyamide moiety replacing the carboxyl moiety of its carboxy terminus (i.e., C-terminus). Accordingly, in its first aspect, the present invention is directed to this compound.

In another aspect, the present invention is directed to a pharmaceutical composition comprising:

(a) a therapeutically effective amount of a compound of the formula:

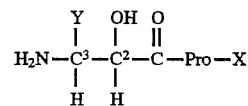

or a pharmaceutically acceptable addition salt thereof,
wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid having a radius of gyration of less than 1.54 Å, X also having a carboxyl or a carboxyamide moiety at its carboxy terminus; and (b) a pharmaceutically acceptable carrier.

In yet another aspect, the present invention is directed to a method for inhibiting bradykinin degradation in a patient comprising: administering to a patient in need of inhibition of bradykinin degradation, (a) a therapeutically effective amount of a compound of the formula:

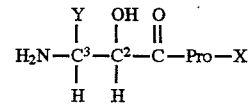

or a pharmaceutically acceptable addition salt thereof,
wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid having a radius of gyration of less than 1.54 Å, X also having a carboxyl or a carboxyamide moiety at its carboxy terminus; and

3

(b) a therapeutically effective amount of an inhibitor to angiotensin converting enzyme.

In the compound, the pharmaceutical composition and the method of the present invention, the first amino acid residue at the N-terminus of X is a natural or a synthetic L-amino acid having a radius of gyration less than 1.54 Å, preferably said first amino acid is Pro, Ala, Ser, Thr, Gly, Vat, Cys or hydroxyproline. In a particularly preferred embodiment, X has 2 amino acid residues. More preferably, X has two amino acid residues and their sequence is -Pro-Ala-NH$_2$, wherein the NH$_2$ at the C-terminus reflects that this oligopeptide has a carboxamide moiety instead of the typical carboxyl moiety at its C-terminus.

BRIEF DESCRIPTION OF THE FIGURES

" FIG. 1A shows a double reciprocal plot (1/v versus 1/S) and the lines represent, in ascending order, the following concentrations of apstatin (µM): 0, 2, 4, 8, 14, 30, 40, 60, 80, 120, 160. FIG. 1B shows the slope replot (●) and 1/v-axis intercept replot (○) of the double reciprocal plot shown in FIG. 1A.

In FIGS. 2A–2C, [$^3$]H-Bk was perfused through the isolated rat lung in the presence or absence of peptidase inhibitors, and the perfusate was analyzed for radiolabelled products by HPLC as described in "Experimental Procedures." Representative chromatograms are shown for perfusate solutions from experiments in which the perfusion medium contained no inhibitors (FIG. 2A); ramiprilat, 0.5 µM (FIG. 2B); and ramiprilat, 0.5 µM plus apstatin, 40 µM (FIG. 2C).

DETAILED DESCRIPTION OF THE INVENTION

Figure 1A:
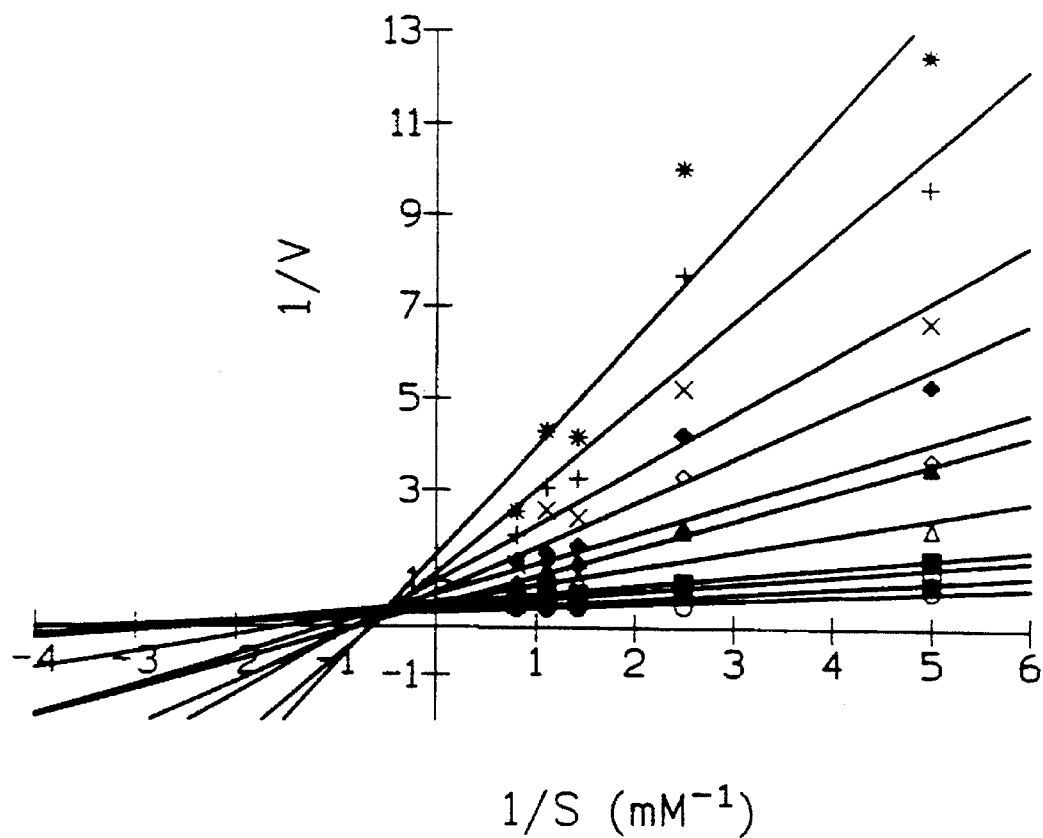
FIGS. 1A and 1B show the kinetics of inhibition of purified bovine lung membrane-bound aminopeptidase P by apstatin where the aminopeptidase P was incubated with various concentrations of substrate (S) (Arg-Pro-Pro) in the presence and absence of various concentrations of apstatin, and the initial velocities (v) were determined as described in "Experimental Procedures.

The present invention has multiple aspects. In its first aspect, it is directed to a compound of the formula:

4

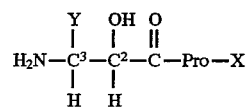

or a pharmaceutically acceptable addition salt thereof,
wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid with a radius of gyration less than 1.54 Angstroms (i.e., Å), X further having a carboxyl or a carboxyamide moiety at its carboxy terminus.

In a particularly preferred embodiment of the compound of the present invention, Y is benzyl or isobutyl; preferably Y is isobutyl.

In the compound of the present invention, the oligopeptide X may include naturally occurring or synthetic amino acid residues. Consistent with convention, the Applicants have utilized herein the three letter abbreviations for the various amino acids and have capitalized the first letter of the amino acid in those instances wherein the amino acid has the "L" configuration, e.g., Pro=L-proline. X also includes amino acids that have the D-configuration.

Any amino acid residues that are utilized in the compound of the present invention as the first amino acid at the N-terminus of X should have the L-configuration and should not be so large as to preclude the compound of the present invention from binding to the active site of aminopeptidase P. A convenient measure for determining whether the first amino acid at the N-terminus of X will be sufficiently small to allow the inhibitor of the present invention to fit within the active site of the enzyme is the radius of gyration such as reported by Levitt et al., (1976) *J. Mol. Biol.*, 104, 59–107 or Sherman et al., (1985) BioEssays, 3: 27–31. Applicant has determined that when the first amino acid in X is hydroxyproline, which has a radius of gyration slightly greater than 1.25 Å, or is a smaller amino acid, the potential inhibitor fits into the active site of aminopeptidase P, whereas when the first amino acid in X is Leu, which has a radius of gyration of 1.54 Å, the potential inhibitor does not fit into the active site. Accordingly, the first amino acid in X is an amino acid (natural or synthetic) with a radius of gyration that is less than 1.54 Å.

By way of example, the radius of gyration in ascending size (Å) for the various naturally occurring amino acids, are as follows: Gly(–); Ala (0.77); Set (1.08); Cys (1.22); Thr (1.24); Pro (1.25); Val (1.29); Asp (1.43); Asn (1.45); Leu (1.54); Ile (1.56); Gln (1.75); Gh (1.77); His (1.78); Met (1.80); Phe (1.90); Lys (2.08); Tyr (2.13); Trp (2.21); and Arg (2.38). Thus, the first amino acid at the N-terminus of X is preferably a member of the group consisting of Gly, Ala, Ser, Cys, Thr, Pro, Vat and hydroxyproline.

Although X may have from 1 to 8 amino acid residues, the preferred number of amino acid residues in X is 1 to 3, more preferably 2.

The compound of the present invention also includes a pharmaceutically acceptable acid addition salt such as the hydrochloride, hydrobromide, hydroiodide, sulfate, phosphate, acetate, propionate, lactate, maleate, realate, succinate, tartrate and the like. Additionally, the compound of this invention may be administered in a suitable hydrated form.

The compound of the present invention may be prepared by any number of methods known to those skilled in the art. For example, the particular sequence of reactions by which a oligopeptide is joined to N-t-BOC-(2S, 3R)-3-amino-2-hydroxy-4-phenylbutyric acid (i.e., Y=benzyl) to form a compound of the present invention is generally not of critical importance, the sequence being chosen principally for convenience or for maximum yields. Moreover, the choice of activating reagents and conditions for joining amino acids or small peptides is not limited to those specifically described herein. The oligopeptide intermediates that are used in this invention are easily synthesized using techniques well known in the art, including full automated peptide synthesizers, such as disclosed in the Examples. Several procedures are available utilizing different resins, different protected amino acids, and different peptide bond-forming strategies. A typical synthesis begins with the attachment to a solid polymeric support of the N-t-butyloxycarbonyl (BOC)-derivative of the amino acid which is to be the C-terminal residue of the peptide. The support may be, as an example, a 4-chloromethyl resin (if the final peptide is to have a C-terminal carboxyl group) or a 4-methylbenzhydrylamine resin (if the C-terminus is to be a carboxamide). The BOC group is then removed by treatment of the resin with 40% (V/V) trifluoroacetic acid (TFA)/dichloromethane (DCM). Following neutralization of the resin with 10% N,N-diisopropylethylamine (in DCM), the BOC-derivative of the next amino acid is coupled to the $\alpha$-amino group of the C-terminal amino acid in the form of an activated ester preformed with hydroxybenzotriazole (HOBt) and N,N'-dicyclohexylcarbodiimide (DCC) in N-methylpyrrolidone (NMP). Following washing of the resin with NMP, any uncoupled amino groups are capped with 10% acetic anhydride (in DCM). Additional amino acids are then added sequentially in the C-to N-terminal direction by repeated cycles of BOC-group removal, neutralization, coupling of the next BOC-amino acid as the activated ester, and capping. Any trifunctional amino acids are side-chain protected as required. The resulting oligopeptide is then capable of being coupled to a protected intermediate, such as t-BOC-3-amino-3-Y-2-hydroxypropanoic acid, after activation of the latter compounds carboxyl group, such as with benzotriazole-1-yl-oxy-tris-(dimethylamino)-phosphonium hexafluorophosphate. The completed peptide is simultaneously removed from the resin and deprotected by treatment of the resin with anhydrous HF containing anisole. The HF is removed in vacuo and the crude peptide is purified by HPLC. The oligopeptides and compounds of this invention are typically purified by crystallization or by column chromatography.

The addition salts that are within the scope of the compound of the present invention are prepared by reacting a neutral compound of the present invention with an excess of the acid form of the addition salt under precipitating conditions. By way of example, the acetate salt of a compound of the present invention is prepared by reacting a compound of the present invention with a molar excess of acetic acid in a polar solvent, such as methylene chloride, and evaporating the solvent until salt formation occurs.

The compound of the present invention was found to have the ability to inhibit the activity of the enzyme, aminopeptidase P, which is found in the mammalian lung.

Figure 1B:
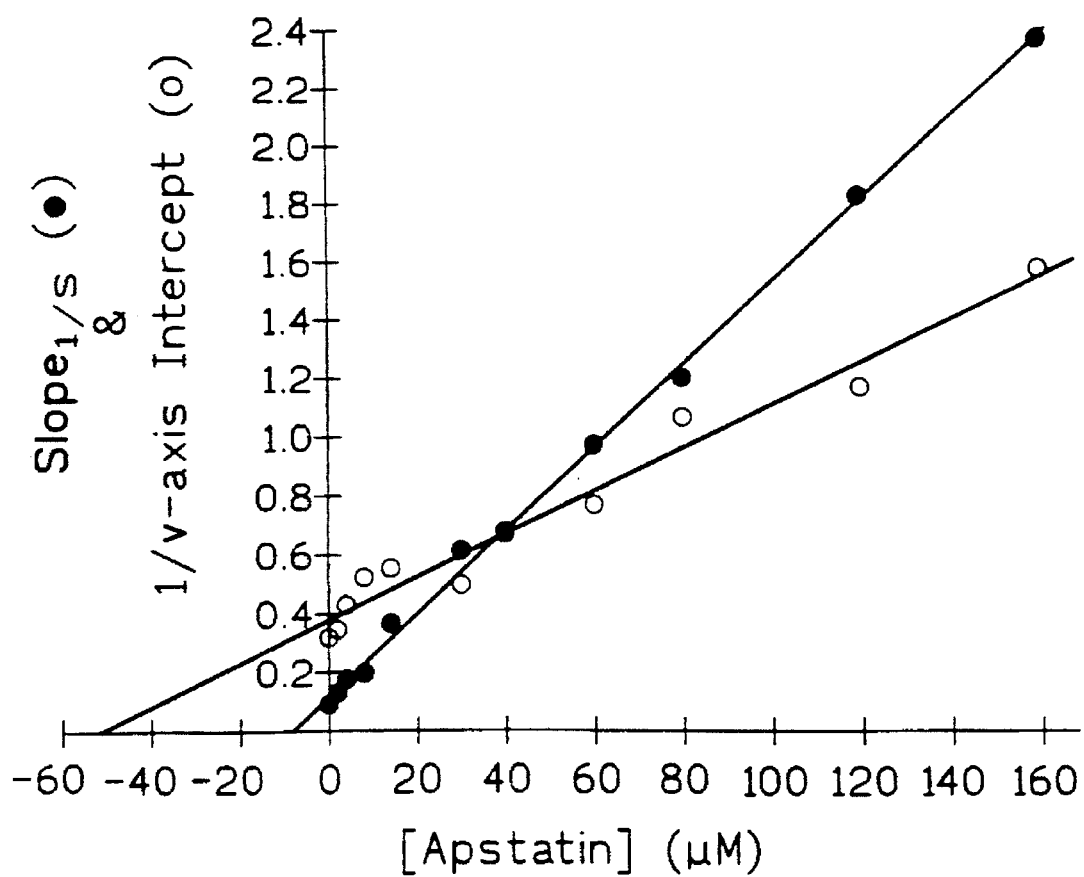

The kinetics of inhibition of one compound of the present invention wherein Y is a benzyl and X is -Pro-Ala-NH$_2$ (hereinafter "apstatin") was determined as described in the Experimental Procedures using Arg-Pro-Pro as the substrate, and purified bovine lung membrane-bound aminopeptidase P as the enzyme. Apstatin exhibited mixed-type kinetics (FIG. 1A). Slope and 1/v-axis intercept replots (FIG. 1B) showed that inhibition was a linear mixed-type with $\alpha>0$ and $\beta=0$. Cf. (28).

The inhibitory constant $K_i$ was determined, as described in the Experimental Procedure herein, from plots of 1/v versus i, wherein i is the concentration ($\mu M$) of inhibitor, while $\alpha K_i$ was determined from s/v versus i, wherein i is the concentration ($\beta M$) of inhibitor. Table 1 compares the $K_i$ and $\alpha$ values for purified bovine and rat lung membrane-bound aminopeptidase P, partially purified human lung membrane-bound aminopeptidase P, and recombinant $E.\ coli$ aminopeptidase P, using apstatin as the inhibitor. All enzymes showed a linear mixed-type inhibition with $K_i$ values in the micromolar range. Table 1 reflects that human aminopeptidase P had the highest affinity for apstatin, having a $K_i=0.64\ \mu M$, compared to 2.6 $\mu M$ for aminopeptidase P of rat origin and 7.8 $\mu M$ for aminopeptidase P of bovine origin.

TABLE 1

Inhibition of Various Aminopeptidase P Preparations by Apstatin

| Source of Aminopeptidase P | $K_i(\mu M)^a$ | $\alpha^b$ |
| --- | --- | --- |
| rat lung$^c$ | 2.6 | 5.1 |
| bovine lung$^c$ | 7.8 | 4.2 |
| human lung$^d$ | 0.64 | 11. |
| E. coli$^e$ | 14. | 2.5 |

$^a$Inhibition in all cases was linear mixed-type ($\beta = 0$). $K_i$ is defined as the equilibrium constant for enzyme-inhibitor binding in the absence of substrate.
$^b\alpha K_i$ is the equilibrium constant for enzyme-inhibitor binding at infinite substrate concentration.
$^c$Purified membrane-bound form.
$^d$Partially purified membrane-bound form.
$^e$Recombinant (22).

Preincubation of rat aminopeptidase P with apstatin for up to 2 hr. at 4° C. before addition of substrate did not increase the degree of inhibition compared with no preincubation, indicating the absence of any time-dependent or slow-tight binding inhibition. A 100-fold dilution of a preincubated enzyme-apstatin mixture led to the degree of inhibition expected from control experiments for the residual apstatin concentration without preincubation, indicating reversibility. Inhibition by apstatin was not dependent on the presence of $Mn^{+2}$.

The IC$_{50}$ of the compound of the present invention in relation to aminopeptidase P was also determined. The IC$_{50}$ is the concentration causing 50% inhibition of the cleavage of 0.5 $\mu M$ Arg-Pro-Pro in 0.1M Hepes, pH 8.0 at 37° C. In particular, the IC$_{50}$ of apstatin for human lung aminopeptidase P was 2.9 $\mu M$; for bovine lung aminopeptidase P, it was 9.4 $\mu M$; and for rat lung aminopeptidase P, it was 4.1 $\mu M$. The specificity of the compound of the present invention for other aminopeptidases was similarly determined as described in the Experimental Procedures herein. In particular, the IC$_{50}$ of apstatin was 600 $\mu M$ for aminopeptidase M and 1,100 $\mu M$ for dipeptidyl-peptidase IV. The following enzymes had IC$_{50}$ values>800 $\mu M$: aminopeptidase A, angiotensin converting enzyme, dipeptidyl-peptidase I-like activity, bestatin-sensitive/amastatin-insensitive membrane dipeptidase (29), microsomal dipeptidase, endopeptidase 24.11, endopeptidase 24.15, and prolyl oligopeptidase. Surprisingly, prolidase, the cytosolic X-Pro-specific dipeptidase, had an IC$_{50}$ value for apstatin of 4.9 $\mu M$.

The IC$_{50}$ was also determined for two stereoisomers of a compound of the present invention wherein Y is isobutyl, X is Pro-Ala-NH$_2$ and C$^2$–C$^3$ are 2S,3R and 2R,3S, respectively. Specifically, the IC$_{50}$ for the two stereoisomers were determined for aminopeptidase P derived from three different sources: rat lung, bovine lung and human lung. This data is reported in Table 2 and reflects that for human lung aminopeptidase P, the 2S,3R stereoisomer exhibited the lowest IC$_{50}$, i.e., 0.23 µM. The IC$_{50}$ of this 2S,3R stereoisomer was approximately ten-fold better than the IC$_{50}$ apstatin (2.9 µM).

TABLE 2

| Aminopeptidase P From | IC$_{50}$ (µM) | |
|---|---|---|
| | (2S,3R)[a] | (2R,3S)[b] |
| rat lung | 0.56 | 0.31 |
| bovine lung | 4.5 | 2.1 |
| human lung | 0.23 | 0.43 |

[a]The (2S,3R) stereoisomer is
N-[(2S,3R)-3-amino-2-hydroxy-5-methylhexanoyl]-L-prolyl-L-prolyl-L-alaninamide.
[b]The (2R,3S) stereoisomer is:
N-[(2R,3S)-3-amino-2-hydroxy-5-methylhexanoyl]-L-prolyl-L-prolyl-L-alaninamide.

Figure 2A:
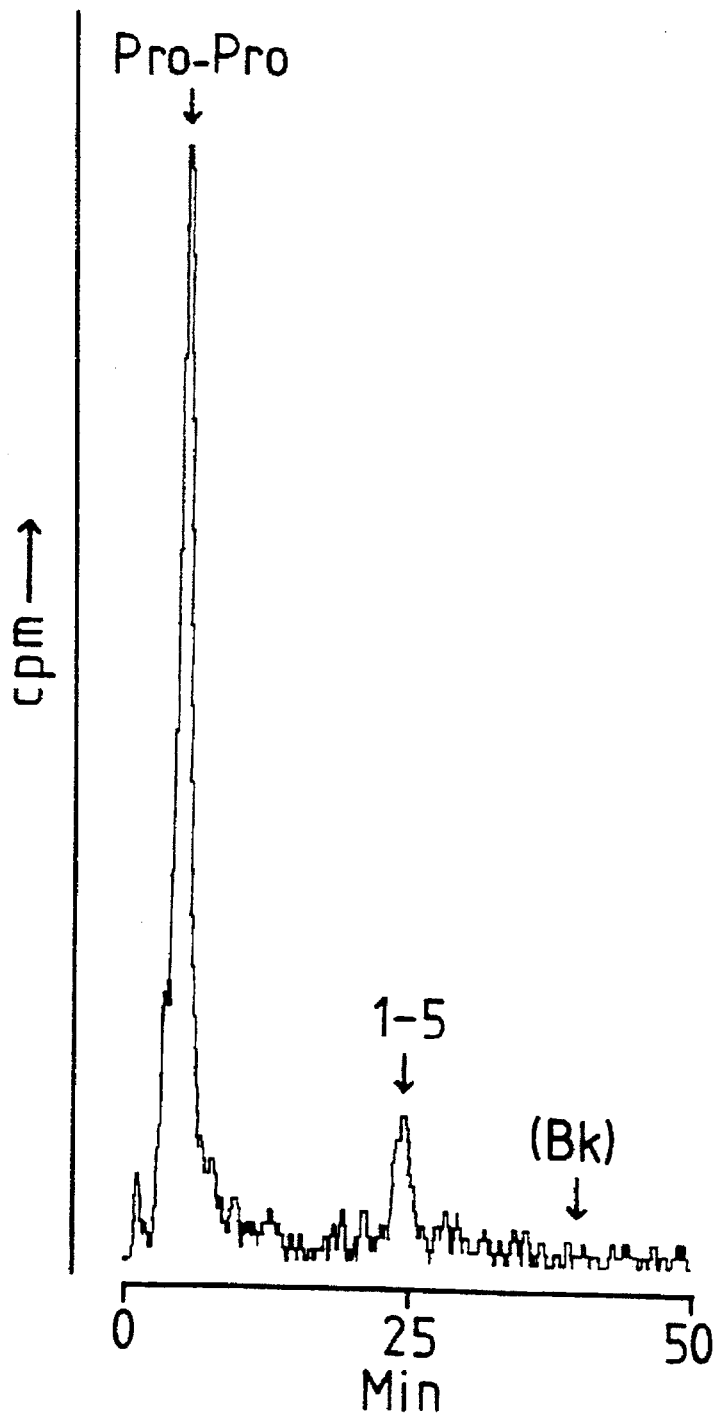
FIGS. 2A–2C show the effects of apstatin and ramiprilat on [$^3$H]-bradykinin degradation in the isolated perfused rat lung.
Figure 2B:
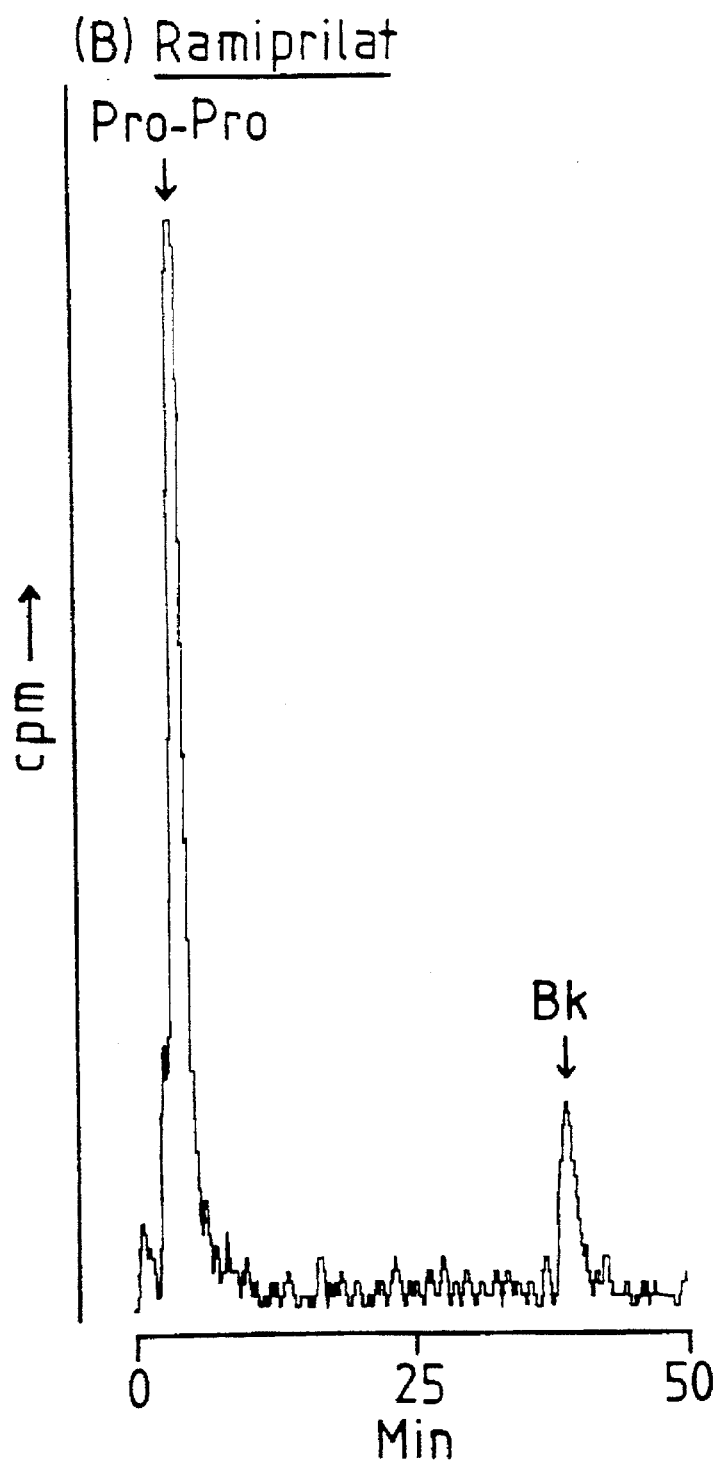
Figure 2C:
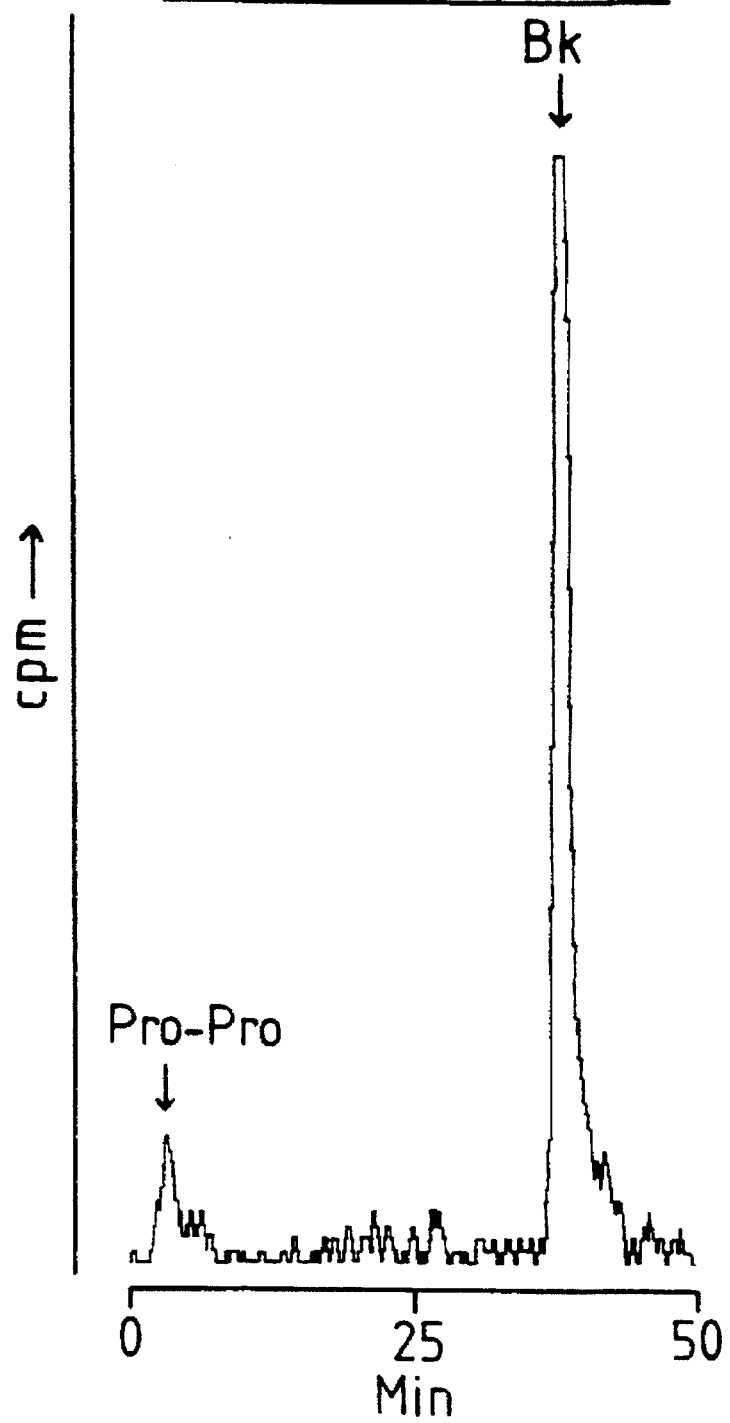
Figure 3:
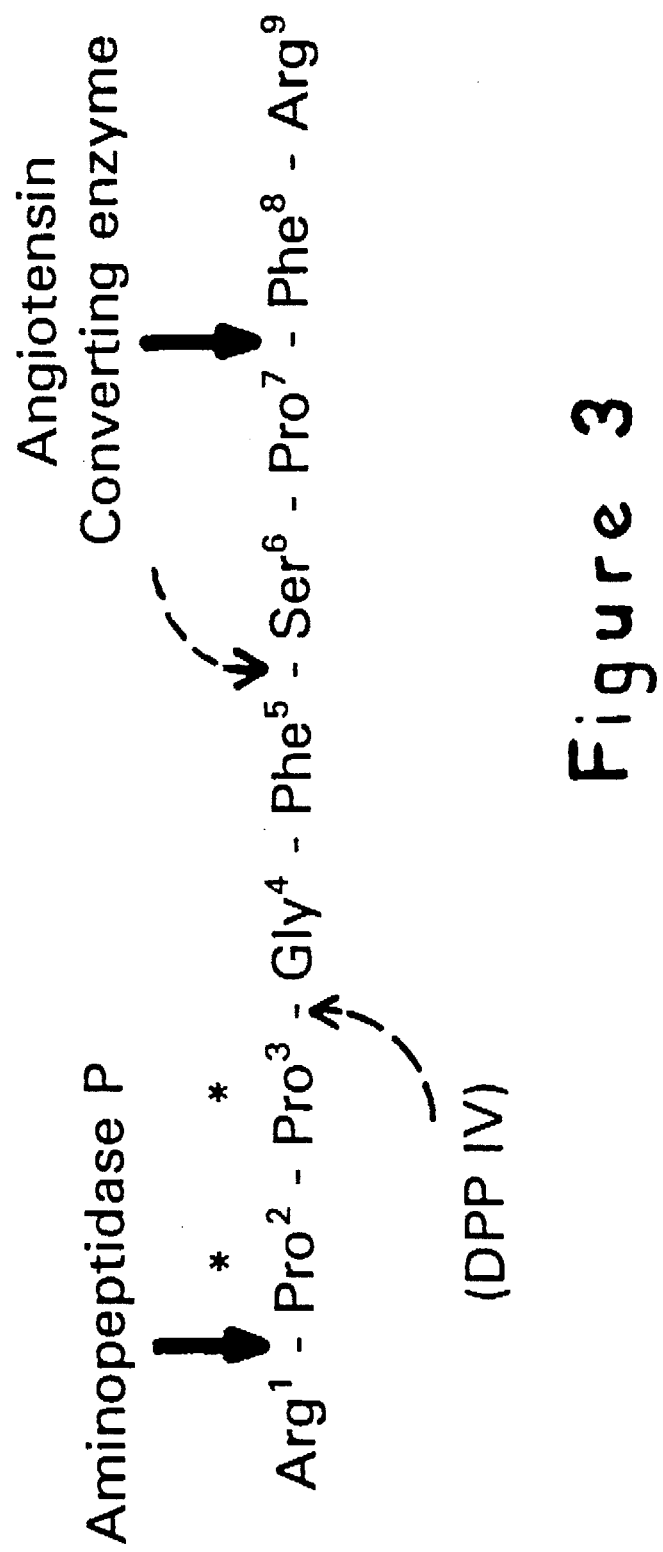
FIG. 3 shows the amino acid sequence of bradykinin ("Bk") and the proposed mechanism of degradation of Bk in the rat pulmonary circulation. The solid arrows represent primary sites of cleavage. The dotted arrows represent bonds which are cleaved only after the corresponding primary cleavages have taken place. DPP IV is dipeptidyl-peptidase IV.

Using the procedure described herein, under Experimental Procedures it was determined that aminopeptidase P contributed to Bk degradation in the mammalian lung. In that procedure, [$^3$H]-Bk (labelled in Pro$^2$ and Pro$^3$) was perfused through the isolated lung in the presence or absence of various peptidase inhibitors. The perfusate was then analyzed for radiolabelled products by HPLC. FIG. 2A shows that when [$^3$H]-Bk was perfused in the absence of inhibitors, no intact Bk was found in the perfusate. This is consistent with previous data demonstrating almost complete degradation of Bk during a single passage through the rat pulmonary circulation (8–10, 17). Most of the radioactivity (an average of 79%) was in the form of [$^3$H]-Pro-Pro [Bk(2–3)] with the remainder being [$^3$H]-Bk(1–5). It was hypothesized that pulmonary vascular aminopeptidase P was cleaving the Arg$^1$-Pro$^2$ bond followed by rapid removal of Pro-Pro by dipeptidylpeptidase IV (DPP IV) (12). These cleavage sites on Bk are shown in FIG. 3. Simultaneously, angiotensin converting enzyme (ACE) was sequentially removing Phe-Arg and Ser-Pro from the C-terminus (13). To test this hypothesis, [$^3$H]-Bk was perfused in the presence of an ACE inhibitor ramiprilat (FIG. 2B), or in the presence of ramiprilat plus apstatin (FIG. 2C). FIG. 2B shows that ramiprilat alone blocked the formation of [$^3$H]-Bk(1–5) and gave rise to a comparably sized peak of intact [$^3$H]-Bk. However, most of the radioactivity remained in the Pro-Pro peak indicating substantial cleavage of Bk at the N-terminal end. When a DPP IV inhibitor, diprotin A, was present along with ramiprilat (data not shown) most of the radioactivity eluted from the lung in the form of [$^3$H]-Bk(2–9). This indicated that in the presence of ramiprilat, the primary site of cleavage was at the Arg$^1$-Pro$^2$ bond and that [$^3$H]-Pro-Pro arose by DPP IV cleavage of [$^3$H]-Bk(2–9). FIG. 2C shows that when apstatin and ramiprilat were present together, cleavage at both the N-terminal and C-terminal end was blocked, and most of the radioactivity eluted as intact [$^3$H]-Bk. Only a small peak of [$^3$H]-Pro-Pro remained which was presumably due to incomplete inhibition of aminopeptidase P at 40 µM apstatin (which is only fifteen times the K$_i$ concentration).

Figure 4:
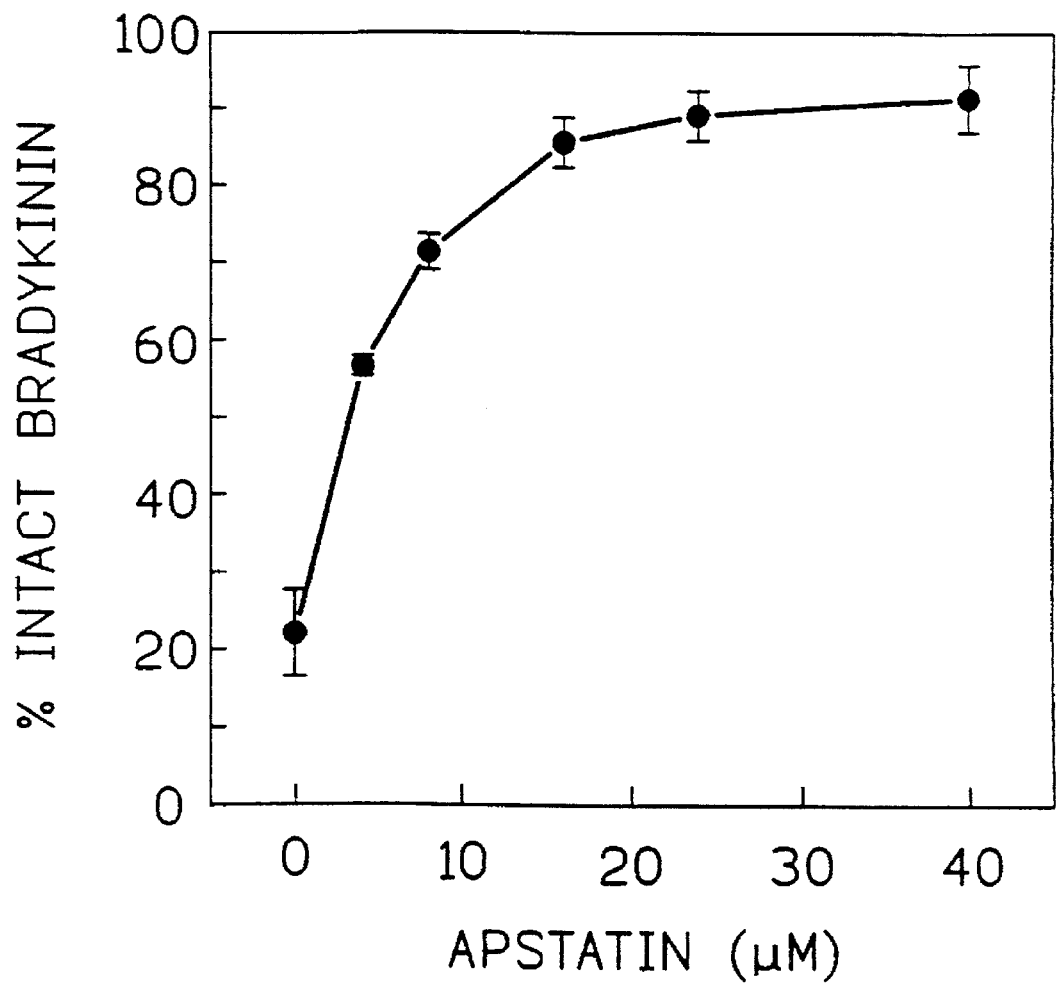
FIG. 4 shows the effect of apstatin concentration on the survival of bradykinin (Bk) in the isolated perfused rat lung. Isolated rat lungs were perfused with [$^3$H]-Bk in the presence of either ramiprilat (0.5 µM) alone or in combination with ramiprilat plus various concentrations of apstatin. The percent of total radioactivity present in the perfusate as intact [$^3$H]-Bk was determined by HPLC and plotted as a function of apstatin concentration. The results are given as the mean (± Standard Error of the Mean, i.e., "SEM") of values obtained from three different rats.

FIG. 4 shows the percentage of the radioactivity surviving as intact [$^3$H]-Bk as a function of apstatin concentration in the presence of ramiprilat. An average of 22±6% of the radioactivity eluting from the lung was intact [$^3$H]-Bk when ramiprilat alone was present in the perfusion medium. When increasing concentrations of apstatin were included along with ramiprilat, the percentage of intact [$^3$H]-Bk eluting from the lung increased. At 40 µM apstatin, 92±4% of the radioactivity was [$^3$H]-Bk.

The above results reflect that aminopeptidase P and ACE can fully account for the degradation of Bk in the pulmonary circulation of the rat as shown in FIG. 4. Other membrane-bound aminopeptidases, namely aminopeptidases A and M, cannot degrade intact Bk (37). In control experiments, a potent inhibitor of these enzymes, [(2S, 3R)-3-amino-2-hydroxy-5-methylhexanoyl]-Val-Val-Asp, also called amastatin (38) had no significant effect on the pattern of metabolites when present at 100 µM along with ramiprilat in the perfusion medium (data not shown).

Earlier in vitro studies using rat lung microsoma/membranes had indicated that endopeptidase 24.11 was present in the lung and could make a minor contribution to Bk degradation by this preparation by hydrolyzing the Pro$^7$-Phe$^8$ bond (13). However, no [$^3$H]-Bk(1–7) was observed in the perfusate when apstatin and ramiprilat were present suggesting that the endopeptidase 24.11 is not involved in the pulmonary degradation of Bk in vivo. Endopeptidase 24.11 has been found immunocytochemically on lung epithelial cells but not on lung vascular endothelial cells that would be in direct contact with circulating Bk (39–40).

Overall, aminopeptidase P was quantitatively less important than ACE in degrading Bk in the perfused rat lung. The ACE inhibitor ramiprilat alone increased the amount of intact [$^3$H]-Bk eluting from the lung from unmeasurable levels to 22% ($\geq$22-fold). In contrast, apstatin alone (dam not shown) yielded mainly [$^3$H]-Bk(1–5), but increased intact [$^3$H]-Bk to only about 1–3% which was difficult to quantitate accurately. The quantitative role of aminopeptidase P in Bk degradation was shown more clearly when apstatin (at 40 µM) was used together with ramiprilat. The amount of [$^3$H]-Bk in the perfusate increased from 22% with ramiprilat alone to 92% with both inhibitors present, a 4.2 fold increase. Presumably, these values could have been increased toward 100% and 4.5-fold at higher apstatin concentrations.

In order to estimate the relative contributions of aminopeptidase P and ACE to the pulmonary cleavage of BK, the integrated form of the two enzyme/one substrate model (32) under first-order conditions was used as described in the Experimental Procedures. Assuming an overall pulmonary inactivation of Bk (H$_{APP+ACE}$) of 99.75% as recently determined in vivo by Ryan et al. (10), it was calculated that aminopeptidase P is responsible for 25% of the cleavage of Bk while ACE is responsible for 75%. Other assumptions for overall pulmonary activation from 98% (17) to 99.9% gave calculated contributions for aminopeptidase P ranging from 39% to 20%, respectively.

While aminopeptidase P appears to be quantitatively less important than ACE, there is now evidence that aminopeptidase P is nevertheless a physiologically important regulator of the blood pressure response to Bk in the rat (15,41). Apstatin alone was shown to significantly potentiate the magnitude as well as the duration of the blood pressure decrease caused by intravenous administration of Bk. Apstatin plus lisinopril (an ACE inhibitor) was also more effective in this regard than lisinopril alone. Thus, aminopeptidase P appears to play a significant role in the pulmonary degradation of Bk. Further, apstatin has proven itself to be an effective inhibitor of aminopeptidase P and a useful pharmaceutical agent when used in combination with an ACE inhibitor so as to allow Bk to exert its well known and useful effects over a prolonged period of time.

Thus, in its second aspect, the present invention is also directed to a pharmaceutical composition that is capable of inhibiting bradykinin degradation. The pharmaceutical composition of the present invention comprises:

(a) a therapeutically effective amount of a compound of the formula:

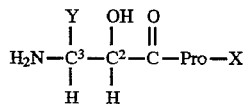

or a pharmaceutically acceptable addition salt thereof, wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid with a radius of gyration less than 1.54 Å, X further having a carboxyl or a carboxyamide moiety at its carboxy terminus; and (b) a pharmaceutically acceptable carrier.

The compound of the present invention is typically administered in a pharmaceutically acceptable carrier. Pharmaceutically acceptable carriers are well known in the art. These carriers may be liquid or solid and include oils, polymers, vitamins, carbohydrates, amino acids, salts, buffers, albumin, surfactants, bulking agents, binding agents and fillers. In liquid formulation, preferred carbohydrates include sugar or sugar alcohols, such as mono, di, or polysaccharides, or water soluble glueans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. "Sugar alcohol" is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferably between 2.0 and 6.0 w/v %. Amino acids include levorotary (L) forms of carnitine, arginine, and betaine; however, other amino acids may be added. Preferred polymers include polyvinylpyrrolidone (PVP) with an average molecular weight between 2,000 and 3,000 daltons, or polyethylene glycol (PEG) with an average molecular weight between 3,000 and 5,000 daltons. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred.

In solid formulations, the compound of the present invention is combined with a filler and a binding agent such as known to the art. Some agents may act both as a filler and a binder. Suitable fillers include one or more polysaccharides, such as the starches, the celluloses, and derivatives thereof, xanthan gum, gum arabic and the like. Suitable binders include any of the binders known to the art. By way of example, a suitable binder is one or more of the carbohydrates mentioned above.

It is also within the scope of the present invention that the compound of the present invention be formulated in a slow release formulation, such as disclosed in U.S. Pat. No. 4,917,893, entitled "Prolonged Release Microcapsules" or in U.S. Pat. No. 4,359,483, entitled "Process for Producing A Multi-Layered Slow Release Compound," both of which are hereby incorporated herein by reference.

The pharmaceutical composition of the present invention is typically administered in oral dosage form such as tablets, capsules, pills, powders, granules, suspensions, or solutions. It may also be administered rectally or vaginally, in such forms as suppositories or bougies. It may also be administered intraperitoneally, subcutaneously, intramuscularly or intravenously using forms known to the pharmaceutical art. In general, the preferred route of administration is oral or intravenous.

In its third aspect, the present invention is directed to a method of inhibiting bradykinin degradation in a mammalian patient comprising: administering to a mammalian patient in need of inhibition of bradykinin degradation, a therapeutically effective amount of a compound of the formula:

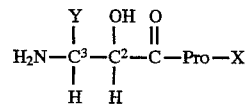

or a pharmaceutically acceptable addition salt thereof, wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid having a radius of gyration less than 1.54 Å, X further having a carboxyl or a carboxyamide moiety at its carboxy terminus.

Optionally, the method of the present invention further includes the step of administering a therapeutically effective amount of an inhibitor to angiotensin converting enzyme.

The method of the present invention comprises coadministering an inhibitor of aminopeptidase P, preferably in combination with an inhibitor of angiotensin convening enzyme (ACE). By the term "coadministering" as used herein, is meant that the aminopeptidase P inhibitor of the present invention and the ACE inhibitor be administered such that both are present in the patient's bloodstream at the same time in therapeutically effective amounts. Thus, it is within the scope of the present invention that both compounds be administered as a single tablet, substantially simultaneously as two tablets, or in other instances, such as where one of the inhibitors has a long half-life in vivo, it may be sufficient that the two compounds be administered within the same forty-eight hour period. Preferably, the pharmaceutical composition of the present invention is administered in unit dosage form. However, regardless of how or when the inhibitors to aminopeptidase P and ACE are administered, the method of the present invention is limited to administering them such that the patient in need of treatment has a therapeutically effective amount of each member of the combination in their bloodstream at any particular time.

An effective but nontoxic quantity of the compound of the present invention is employed in any treatment. The dosage regimen for inhibiting bradykinin degradation by the compound of this invention is selected in accordance with a variety of factors including the type, age, weight, sex and medical condition of the mammal, the severity of the symptoms, and the route of administration of the particular compound employed. A physician or veterinarian of ordinary skill will readily determine and prescribe the therapeutically effective dosage based on the route of administration of the Bk inhibitor to prevent or arrest the progress of the condition. In so proceeding, the physician or veterinarian would employ relatively low dosages at first, subsequently increasing the dose until a maximum response is obtained. Because the compounds of the present invention are excreted through the kidney, patients with impaired renal function would receive a lesser dose than patients with normal renal function. Physicians would assess a patient's renal function by monitoring the patient's serum creatinine. Serum creatinine concentrations increasing above 1.0 mg/dl reflect decreasing renal function. Thus, by the term "therapeutically effective mount" as used herein is meant the amount of the compound that is effective to cause substantial inhibition of its respective enzyme such that the combination substantially increases the half-life of any endogenous Bk that is formed in the patient.

In rats, Bk potentiation by apstatin has been observed with 0.08–0.8 mg/kg intravenously when administered over a one hour period. More potent inhibitors of the present invention, wherein Y=isobutyl, and wherein X is Pro-Ala-NH$_2$ should be effective at five to tenfold lower dosages. See e.g., Table 2. Less potent inhibitors would require a greater dosage to provide the same therapeutic result. A typical therapeutically effective dose of a compound of the present invention is from about 0.008 mg/kg to 8.0 mg/kg, when given intravenously.

Inhibitors of ACE are well known in the art and are used for inhibiting the in vivo conversion of angiotensin I to angiotensin II. Typical inhibitors of ACE include captopril, enalapril, enalaprilat, lisinopril, quirtapril, benazepril, fosinopril, ramipril and ramiprilat. The method of administration and dosages for each of these ACE inhibitors is well known in the art and are disclosed in the 1995 Physician's Desk Reference.

Captopril, which is also known as 1-[(2S)-3-mercapto-2-methyl propionyl]-L-proline, is typically administered to humans as tablets at between 18.75 mg to 150 mg/day with a target of 150 mg/day, but never to exceed 450 mg/day. Enalapfil, which is also known as (S)-1-[N-[1-(ethoxycarbonyl)-3-phenylpropyl)]-L-alanyl]-L-proline, (Z) maleate (1:1), is typically administered to human patients as tablets at between 10 mg/day to 25 mg/day, not to exceed 50 mg/day. Enalapril is convened in vivo to enalaprilat, the acid form enalapril. Enalaprilat has the formula: (S)-1-[N-(1-carboxy-3-phenylpropyl)-L-alanyl]-L-proline dihydrate and is typically administered intravenously. Lisinopril, which is also known as (S)-1-[N$^2$-(1-carboxy-3-phenylpropyl)-L-lysyl]-L-proline dihydrate, is typically administered to human patients as tablets at a dosage of 20 mg/day to 40 mg/day. Ramipril, which is also known as (2S,3aS,6aS)-I[ (S)-N-[(S)-1-carboxy-3-phenylpropyl]alanyl] octahydrocyclopenta[b]pyrrole-2-carboxylic acid, 1-ethylester, is converted in vivo to its aliacid form ramiprilat. Ramipril is administered as tablets with the typical dosage for human patients of 2.5 mg/day to 20 mg/day.

In the process of the present invention, a physician or veterinarian would coadminister the ACE inhibitor component of the present invention at the above described dosages, allowing for variations due to the patient's weight, health, age, and renal condition. For example, serum creatinine concentration increasing above 1.0 mg/dl reflect decreasing renal function and a decreased ability to excrete the inhibitors used in the method of the present invention. However, in each instance, the patient is administered therapeutically effective amount, i.e. , an amount sufficient to substantially inhibit the cleavage of Bk by ACE, and to substantially inhibit the cleavage of Bk in vivo when administered in conjunction with an inhibitor of aminopeptidase P as already discussed above.

Because Bk is known to decrease blood pressure, dilate the coronary arteries, protect the heart during myocardial ischemia reperfusion injuries, enhance renal function, and improve glucose tolerance and insulin sensitivity (2), the present invention is further directed to a method for obtaining any one of these effects comprising administering to a patient in need of one of the above effects, a therapeutically effective amount of a compound of the formula:

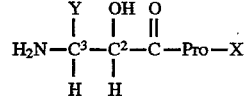

or a pharmaceutically acceptable addition salt thereof, wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid .with a radius of gyration of less than 1.54 Å, X also having a carboxyl or a carboxyamide moiety at its carboxy terminus.

The above methods of the present invention may further include the step of coadministering to said patient a therapeutically effective amount of an inhibitor to angiotensin converting enzyme, such as already discussed herein.

Experimental Procedures

Materials—[2,3-Prolyl-3,4-$^3$H(N)]-bradykinin (lot 3109-298) was obtained from Dupont NEN Research Products (Boston, Mass.). The specific activity was 62.0 Ci/mmol and the purity as shipped was 97.1%. Ramiprilat was the girl of Dr. Ronald J. Shebuski (The Upjohn Company, Kalamazoo, Mich.). Arg-Pro-Pro and cyclo-Pro-Pro were obtained from Bachera Bioscience (Philadelphia, Pa.). Ile-Pro-Ile (diprotin A), amastatin, and N-t-BOC-(2S,3R)-3-amino-2-hydroxy-4-phenylbutanoic acid were obtained from Sigma (St. Louis, Mo.). Purified rat lung aminopeptidase P was used to enzymatically produce the following fragments of the bradykinin ("Bk") nonapeptide: Bk(2–5) from Bk(1–5), Bk(2–6) from Bk(1-6), and Bk(2-8) from Bk(1-8). All other Bk-fragment standards were obtained from sources indicated in references (12, 14, 19, 21 herein.) For convenience, any prior art references to procedures used in the Applicants' Experimental Procedures are parenthetically referred to herein by number and numerically listed at the end of the Detailed Description.

Enzymes—Membrane-bound aminopeptidase P was purified to homogeneity from bovine lung (14) and from rat lung. Partially purified membrane-bound aminopeptidase P from human lung was obtained by treatment of lung microsomes with phosphatidylinositol-specific phospholipase C (*B. thuringiensis*) (ICN, Costa Mesa, Calif.) followed by centrifugation as described previously (14). Membrane dipeptidase was purified from rat lung microsomes (manuscript in preparation). Recombinant *E. coli* aminopeptidase P (22) and purified lamb kidney prolyl oligopeptidase (23) were generally supplied by Dr. Tadashi Yoshimoto (Nagasaki University). Purified porcine kidney prolidase and purified porcine kidney aminopeptidase M was obtained from Sigma (St. Louis, Mo.).

Synthesis of N-[(2S, 3R)-3-amino-2-hydroxy-4-phenylbutanoyl]-L-prolyl-L-prolyl-L-alaninamide (Apstatin) —The tripeptide, Pro-Pro-Ala-NH$_2$, was prepared on resin by standard solid-phase techniques (24) using an Applied Biosystems 430A peptide synthesizer beginning with p-methylbenzhydrylamine resin. The N-t-BOC-(2S,3R)-3-amino-2-hydroxy-4-phenylbutyric acid was coupled to the tripepride-resin in a manual apparatus using benzotfiazole-1-yl-oxy-tris-(dimethylamino)-phosphonium hexafluorophosphate (BOP) as an activating agent (25). The N-terminal BOC group was removed with 40% trifluoroacetic acid (TFA) in methylene chloride, and the peptide was cleaved from the resin by treatment at 0° C. with HF-anisole (9/1) for one hour. Crude peptide was extracted from the resin with 50% aqueous acetic acid and lyophilized. It was purified by preparative reversed-phase HPLC on a Vydac C$_{18}$ column with a linear gradient beginning with 100% water (0.1% TFA) to 80% water/20 % acetonitrile (0.1% TFA). After lyophilization the purified peptide showed a single peak on analytical HPLC on a Vydac C$_{18}$ column. It was characterized by fast atom bombardment mass spectrometry and showed a [M+H]$^+$ ion at m/z 460.

Synthesis of N-[(2S,3R)-3-amino-2-hydroxy-5-methylhexanoyl]-L-prolyl-L-prolyl-L-alaninamide—This compound is prepared as described above for apstatin replacing N-t-BOC-(2S,3R)-3-amino-2-hydroxy-4-phenylbutyric acid with N-t-BOC-(2S-,3R)-3-amino-2-hydroxy-5-methylhexanoic acid (Sigma Chemical Co., St. Louis, Mo.; Cat. No. B 8020).

Synthesis of N-[(2R,3S)-3-amino-2-hydroxy-5-methylhexanoyl]-L-prolyl-L-prolyl-L-alaninamide—This compound is prepared, as described above for apstatin, replacing N-t-BOC-(2S,3R)-3-amino-2-hydroxy-4-phenylbutyric acid with N-t-BOC-(2R,3S)-3-amino-2-hydroxy-5-methylhexanoic acid.

Synthesis of N-t-BOC-(2S,3R)-3-amino-3-Y-2-hydroxypropanoic acid or N-t-BOC-(2R,3S)-3-amino-3-Y-2-hydroxypropanoic acid A benzyloxycarbonyl-[Z-] protected amino acid is used as the starting material. The amino acid is a natural or unnatural α-amino acid with a side-chain of Y in either the D-configuration [for inhibitors having the (2S ,3R)-stereochemistry] or the L-configuration [for inhibitors having the (2R,3S)-stereochemistry]. To the Z-amino acid in ethyl acetate is added one equivalent of dicyclohexylcarbodiimide. Thirty minutes after addition, one equivalent of pyrazole is added and the mixture stirred for sixteen hours at 0° C. After removal of dicyclohexylurea by filtration, the solvent is evaporated and the pyrazolide of the Z-amino acid (compound "1") is crystallized from ethyl acetate. To a solution of 1 in dry tetrahydrofuran (THF) at -20° C. is added two equivalents of LiAlH$_4$ in THF over a period of 45 minutes followed by stirring at the same temperature for one hour. Excess reagent is then decomposed by the slow addition of 5N HCl. The solvent is evaporated and the residue extracted with ethyl acetate. The extract is washed with water and then dried to yield the benzyloxycarbonyl-amino acid aldehyde ("2"). An aqueous suspension of 2 is treated with two equivalents of NaHSO$_3$ at 60° C. for two hours to form the NaHSO$_3$ adduct ("3") which is then extracted with ethyl acetate followed by removal of the solvent by evaporation. To an aqueous suspension of 3 is added 1 equivalent of NaCN over a period of 1 hour to form the cyanohydrin ("4"). Compound 4 is extracted with ethyl acetate and the solvent evaporated. Compound 4 is then hydrolyzed by refluxing in 6N HCl to give 3-amino-3-Y-2-hydroxy-propanoic acid ("5") as a mixture of diastereoisomers [either (2S,3R) and (2R,3R) or (2S,3S) and (2R,3S) depending on whether the starting material was the D-amino acid or L-amino acid, respectively]. The diastereoisomers are then separated by chromatography on Dowex 50WX4 using 0.1M pyridine-formic acid (pH 3.1). The (2S,3R) or (2R,3S) isomer of compound 5 is then converted to the N-t-BOC derivative by reaction with 2-t-butyloxycarbonyloximino-2-phenylacetonitrile in aqueous 1,4-dioxane containing triethylamine [Bodanszky, M. and Bodanszky, A. (1984), *The Practice of Peptide Synthesis*, Springer-Verlag, Berlin]. The resulting t-BOC-(2S,3R)-3-amino-3-Y-2-hydroxypropanoic acid or t-BOC-(2R,3S)-3-amino-3-Y-2-hydroxypropanoic acid is then coupled to the Pro-X-resin as described for apstatin.

Enzyme Kinetics—Aminopeptidase P activity was determined by measuring the release of arginine from Arg-Pro-Pro by a fluorescent assay described previously (14). The effect of apstatin on aminopeptidase P kinetics was determined by incubating the enzyme with various concentrations of Arg-Pro-Pro (0.2–1.25 mM), each in the presence of various concentrations of apstatin (0–160 μM), in 0.1 M Hepes, pH 8.0, at 39° C. Each mixture was run in duplicate. Aliquots were removed from each incubation mixture at various times and assayed for the amount of arginine present to determine the reaction velocity. In general, reaction velocities were calculated from data representing less than 20% cleavage of substrate. $K_i$ and $K_i'$ ($=\alpha K_i$) were determined from plots of 1/v versus concentration of inhibitor "i" (26) and S/v versus concentration of inhibitor "i" (27), respectively. These parameters were also determined from the slope replot and 1/v-intercept replot, respectively, of the 1/v versus 1/S plot (28). See e.g., FIG. 1B. The values from the two treatments of the data were averaged for each experiment. Experiments for each enzyme preparation were performed twice and the results averaged.

Specificity of Apstatin—Apstatin was assayed for its ability to inhibit several other peptidases. The concentration of apstatin needed to cause 50% inhibition of enzyme activity (IC$_{50}$) was determined in each case. Unless otherwise indicated, the source of each enzyme activity was a detergent extract of bovine lung prepared as described in (12–13). Activities were determined by a modification of the fluorescent assay described above (indicated by "FLUO") or by HPLC separation and quantitation of reaction products using the method described in (12) (method "HPLC-1") or the method described below (method "HPLC-2"). The enzymes, substrates, assay conditions, and detection methods were as follows: aminopeptidase A (EC 3.4.11.7) (rat lung microsomes), 1 mM α-Glu-β-Na, 0.1M potassium phosphate ("KPhos") containing 1.1 mM $CaCl_2$ (pH 6.8), HPLC-1; aminopeptidase M (EC 3.4.11.2) (purified, porcine kidney), 0.6 mM Ala-β-NA, 0.1 M KPhos (pH 6.8), by FLUO; ACE (EC 3.4.15.1), 0.5 mM Hip-His-Leu, 0.1M Hepes containing 0.3M NaCl (pH 6.5), HPLC-1; dipeptidyl-peptidase 1-like activity CEC 3.4.14:1) (13), 0.5 mM Gly-Phe-β-naphthalarnide ("Gly-Phe-β-NA"), 0.1M Hepes (containing 10 μM NaCl, 12 μM 2-mercaptoethanol, 0.17 mM amastatin, 5.2% DMSO) (pH 6.5), HPLC-2; dipeptidyl-peptidase IV (EC 3.4.14.5), 0.5 nM Gly-Pro-β-NA, 0.1M KPhos (pH 6.8), FLUO; bestatin-sensitive/amastatin-insensitive membrane dipeptidase (29) (bovine lung microsomes), 0.5 mM Arg-Trp, 0.1M KPhos containing 0.17 mM amastatin (pH 6.8), FLUO; membrane dipeptidase (EC 3.4.13.19) (purified, rat lung), 0.5 mM Gly-D-Phe, 0.1M Hepes containing 20 μM $ZnCl_2$ (pH 8.0), HPLC-1; endopeptidase 24.11 (EC 3.4.24.11), 1 mM Suc-Ala-Ala-Phe-7-amido-4-methyl-coumarin, 0.1M KPhos containing 0.17 mM amastatin (pH 6.8), HPLC-1; endopeptidase 24.15 (EC 3.4.24.15) (rat brain synaptosomes)(21), 1 mM Bk(2–9), 0.1M KPhos (containing 50 μM phosphoramidon, 20 μM captopril, and 1 mM diprotin A) (pH 6.8), HPLC-1; prolyl oligopeptidase (EC 3.4.21.26) (purified, lamb kidney), 0.5 mM Bk, 0.1M KPhos (containing 1 mM EDTA and 0.5 mM 2-mercaptoethanol) (pH 6.8), HPLC-1; prolidase (EC 3.4.13.9) (purified, porcine kidney), 1 mM Arg-Pro, 0.1M Hepes (pH 8.0), HPLC-2.

Perfusion of the Isolated Rat Lung—Male Sprague Dawley rats, weighing 300–500 grams, were anesthetized with sodium pentobarbital (50–75 mg/kg) given by intraperitoneal injection. The trachea was cannulated and the lungs ventilated with air at 70 cycles per minute (Harvard Small Animal Ventilator) at a pressure of 70 mm $H_2O$. The heart and lungs were exposed via midsternal incision and 1000 units of heparin were administered intracardially. Polyethylene cannulae were secured into the pulmonary artery and the left ventricle. A modified Krebs buffer (118.5 mM NaCl, 4.7 mM KCl, 1.1 mM $KH_2PO_4$, 1.1 mM $MgSO_4$, 2.5 mM $CaCl_2$, 19.6 mM $NaHCO_3$, 5.6 mM dextrose), which was kept in a 50° C. water bath and aerated with 95% $O_2$-5% $CO_2$ to pH 7.35, was perfused into the pulmonary artery at 35° C. and 2.6 ml/min (LKB Microperplex peristaltic pump). The buffer was circulated through the isolated lung in situ until the effluent was free of blood. The surgical field was maintained at 37° .C with a heat lamp throughout the procedure. Experiments were conducted by introducing [$^3$H]-Bk in the presence or absence of test peptidase inhibitors into the pulmonary circulation via the pulmonary artery and then collecting perfusion effluent from the left ventricular cannula. Ramiprilat (0.5 μM) or ramiprilat plus apstatin (4–40 μM) in the modified Krebs buffer was perfused through the lung for two minutes. The lung was then perfused with 1 μCi [$^3$H]-Bk in 1 ml of the inhibitor solution (giving 16 nM Bk) followed by inhibitor solution alone. Effluent was collected in tubes (0.5 min/fraction) containing 150 μl of 2% TFA. For each lung preparation, 5–6 samples were perfused over a period of about one hour. Control perfusions of [$^3$H]-Bk alone were always carried out before perfusions of samples containing ramiprilat because of the slow reversibility of inhibition of ACE by this compound. Additional experiments involving perfusion of apstatin or diprotin A alone with [$^3$H]-BK were similarly run before ramiprilat-containing samples for the same reason. The effects of the latter two inhibitors were reversible. Occasionally a lung failed to completely degrade the perfused [$^3$H]-Bk in the absence of inhibitors. Only lungs which showed complete cleavage during the control perfusion were used for quantitative analysis.

Separation and Identification of Bradykinin Metabolites—The fractions which were collected from each perfusion sample run were counted for radioactivity, and the fraction having the highest radioactive counts was prepared for HPLC by filtration through a Centricon-10 microconcentrator (Amicon). An aliquot of the filtrate containing 25000 dpm (approx. 25 μl) was spiked with a cocktail of unlabelled Bk fragments (3 μl) and then subjected to HPLC using a Waters Radial Compression Separation System with a 5μ NOVA PAK $C_{18}$ Radial Pak Cartridge. The column was developed at a flow rate of 1 ml/min with a 60 min linear gradient from 100% Solvent A (0.1% TFA in water) to 75% Solvent A: 25% Solvent B (0.08% TFA in acetonitrile) using a Spectra Physics 8700XR Solvent Delivery System. The column effluent was simultaneously monitored for absorbance at 206 nm (LKB Uvicord S) and for radioactivity (Radiomatic Flo-One HS Radioactive Flow Detector using Ultima-Flo M scintillation fluid from Packard, Meriden, Conn.). The results were displayed on an LKB 2-channel chart recorder, with the radioactive counts indicated at six-second intervals. Radioactive peaks were identified by comparison of the retention times to those of the unlabelled standards. The digital output from the radioactive flow detector was used to calculate the percentage of dpm present in each Bk metabolite. The HPLC method gave the following retention times in minutes for the indicated Bk fragments which contain the position 2 and/or 3 proline residues: Pro,~0; Bk(1–2), 1.4; Bk(2–3), 4.3; Bk(2–4), 5.5; Bk(1–3), 6.4; Bk(1–4), 6.9; cyclo-Pro-Pro, 8.2; Bk(2–6), 19.1; Bk(1–6), 20.9; Bk(2–5), 23.4; Bk(1–5), 24.8; Bk(2–7) 27.2; Bk(1–7), 27.9; Bk(1–9), 41.1; Bk(2–9), 44.4; Bk(1–8), 45.5; and Bk (2–8), 49.7 minutes.

Calculation of the Relative Rates of Bk Degradation by Aminopeptidase P and ACE—An estimation of the relative rates of cleavage of Bk by aminopeptidase P and ACE in the isolated perfused lung was calculated based on assumptions concerning the extent of degradation of Bk in the absence of inhibitors. Degradation of Bk in the perfused lung was assumed to follow Michaelis-Menten kinetics (30) and to be first-order since the concentration of [$^3$H]-Bk (16 nM) was very much less than the $K_m$ value for either aminopeptidase P or ACE (14, 31). The first-order rate constant for the cleavage of Bk by aminopeptidase P [$(V_{max}/K_m)_{APP}$] is given by Equation 1:

$$\left(\frac{V_{max}}{K_m}\right)_{APP} = \frac{1}{t} \ln \frac{100}{100 - H_{APP}} \quad \text{(Eq. 1)}$$

where t is the time of perfusion (capillary transit time) and $H_{APP}$ is the % hydrolysis of Bk at time t when ACE is completely inhibited, i.e., when aminopeptidase P is the only active enzyme (78%, see below). Equation 2 is the integrated form of the equation describing two enzymes acting on a single substrate (32) under first-order conditions.

$$\left[\left(\frac{V_{max}}{K_m}\right)_{APP} + \left(\frac{V_{max}}{K_m}\right)_{ACE}\right] = \frac{1}{t} \ln \frac{100}{100 - H_{APP+ACE}} \quad \text{(Eq. 2)}$$

where $(V_{max}/K_m)_{ACE}$ is the first-order rate constant for ACE. $H_{APP+ACE}$ is the % hydrolysis of Bk at time t when both enzymes are hydrolyzing Bk simultaneously (no inhibitors present). Since $H_{APP+ACE}$ approached 100% and could not be determined accurately, different estimates of $H_{APP+ACE}$ were used based on in vivo experiments (see below). The relative contribution of aminopeptidase P to the overall cleavage of Bk in the isolated perfused lung is given by the ratio of $(V_{max}/K_m)_{APP}$ to $[(V_{max}/K_m)_{APP}+(V_{max}/K_m)_{ACE}]$, Equation 1 divided by Equation 2. In this ratio, the unknown quantity t disappears.

REFERENCES

1. Carretero, O. A. and Scicli, A. G. (1990) in *Hypertension: Pathophysiology, Diagnosis, and Management* (Laragh, J. H. and Brenner, B. M., eds.) pp. 805–817, Raven Press, Ltd., N.Y.
2. Bhoola, K. D., Figueroa, C. D., and Worthy, K. (1992) *Pharmacological Rev.* 44, 1–80.
3. Linz, W., Martorano, P. A., and Scholkens, B. A. (1990) *J. Cardiovasc. Pharmacol.* 15 (Suppl. 6), S99–S109.
4. Pelc, L. R., Gross, G. J., and Waritier, D. C. (1991) *Circulation* 83, 2048–2056.
5. Hartman, J. C., Wall, T. M., Hullinger, T. G., and Shebuski, R. J. (1993) *J. Cardiovasc. Pharmacol.* 21, 996–1003.
6. Linz, W., Wiemer, G., and Scholkens, B. A. (1993) *J. Cardiovasc. Pharmacol.* 22 (Suppl. 9), S1–S8.
7. Wall, T. M., Sheehy, R., and Hartman, J. C. (1994) *J. Pharmacol., Exper. Thera.* 270, 681–689.
8. Ryan, J. W., Roblero, J., and Stewart, J. M. (1970) *Adv. Exp. Med. Biol.* 8, 263–271.
9. Bonner, G., Preis, S., Schunk, U., Toussaint, C., and Kaufmann, W. (1990) *J. Cardiovasc. Pharmacol.* 15 (Suppl. 6), S46–S56.
10. Ryan, J. W., Berryer, P., Chung, A. Y. K., and Sheffy, D. H. (1994) *J. Pharmacol. Exper. Thera.* 269, 941–947.
11. Ryan, J. W. (1989) *Am. J. Physiol.* 257, L53–L60.
12. Orawski, A. T., Susz, J. P., and Simmons, W. H. (1987) *Mol. Cell. Biochem.* 75, 123–132.
13. Orawski, A. T., Susz, J. P., and Simmons, W. H. (1989) *Adv. Exp. Med. Biol.* 2478, 355–364.
14. Simmons, W. H. and Orawski, A. T. (1992) *J. Biol. Chem.* 267, 4897–4903.
15. Kitamura, S., Carbini, L. A., Carretero, O. A., Simmons, W. H., and Scicli, A. G. (1995) *Br. J. Pharmacol.* 114, 6–7.
16. Baker, C. R. F., Jr., Little, A. D., Little, G. H., Canizaro, P. C., and Behal, F. J. (1991) *Cir. Shock* 33, 37–47.
17. Pesquero, J. B., Jubilut, G. N., Lindsey, C. J., and Paiva, A. C. M. (1992) *J. Hyperten.* 10, 1471–1478.
18. Pasquero, J. B., Boschov, P., Lindsey, C. J., and Paiva, A. C. M. (1992) *J. Hyperten,* 10, 1479–1484.
19. Yoshimoto, T., Orawski, A. T., and Simmons, W. H. (1994) *Arch. Biochem. Biophys.* 311, 28–34.
20. Prechel, M. M., Orawski, A. T., and Simmons, W. H. (1994) *The 10th International Conference on IntraceHular Protein Catabolism* (Tokyo).
21. Orawski, A. T. and Simmons, W. H. (1989) *Peptides* 10, 1063–1073.
22. Yoshimoto, T., Murayama, N., Honda, T., Tone, H., and Tsuru, D. (1988) *J. Biochem.* 104, 93–97.
23. Koida, M. and Waiter, R. (1976) *J. Biol. Chem.* 251, 7593–7599.
24. Stewart, J. M. and Young, J. D. (1984) *Solid Phase Peptide Synthesis,* 2nd Ed., Pierce Chemical Company, Rockford, Ill.
25. Castro, B., Dormoy, J. R., Evin, G., and Selve, C. (1976) in *Peptides* 1976 (Loffet, A., ed.) pp. 79–84, Univ. of Brussels.
26. Dixon M. (1953) *Biochem. J.* 55, 170–171.
27. Comish-Bowden, A. (1974) *Biochem. J.* 137, 143–144.
28. Segel, I. H. (1975) *Enzyme Kinetics,* pp. 170–178, John Wiley and Sons, N.Y.
29. Orawsld, A. T. and Simmons, W. H. (1992) *Neurochem. Res.* 17, 817–820.
30. Ryan, J. W. (1983) *Biochem. Pharmacol.* 32, 2127–2137.
31. Dorer, R. E., Kahn, J. R., Lentz, K. E., Levine, M., and Skeggs, L. T. (1974) *Cir. Res.* 34, 824–827.
32. Segel, I. H. (1975) *Enzyme Kinetics,* pp. 64–71, John Wiley and Sons, N.Y.
33. Hooper, N. M., Hryszko, J., Oppong, S. Y., and Turner, A. J. (1992) *Hypertension* 19, 281–285.
34. Umezawa, H., Aoyagi, T., Suda, H., Hamada, M., and Takeuchi, T. (1976) *J. Antibiotics* 29, 97–99.
35. Burley, S. K., David, P. R., Sweet, R. M., Taylor, A., and Lipscomb, W. H. (1992) *J. Mol. Biol.* 224, 113–140.
36. Schecter, I. and Berger, A. (1967) *Biochem. Biophys. Res. Commun.* 27, 157–162.
37. Ward, P. E. (1991) in *Bradykinin Antagonists, Basic and Clinical Research* (Burch, R. M., ed.) pp. 147–170, Marcel Dekker, N.Y.
38. Tieku, S. and Hooper, N. M. (1992) *Biochem. Pharmacol.* 44, 1725–1730.
39. Johnson, A. R., Ashton, J., Schulz, W. W., and Erdos, E. G. (1985) *Am. Rev. Respir. Dis.* 132, 564–568.
40. Ronco, P., Pollard, H., Galceran, M., Delauche, M., Schwartz, J. C., and Verhoust, P. (1988) *Lab. Invest.* 58, 210–217.
41. Kitmura, S., Carbini, L. A., Carretero, O. A., Simmons, W. H., and Scicli, G. (1994) *Hypertension* 24, 396.

I claim:

1. A compound of the formula:

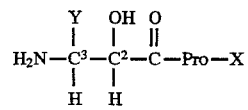

or a pharmaceutically acceptable addition salt thereof, wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid with a radius of gyration of less than 1.54 Å, X also having a carboxyl or a carboxyamide moiety at its carboxy terminus.

2. The compound of claim 1 wherein X is an oligopeptide having 2 amino acid residues.

3. The compound of claim 2 wherein X is -Pro-Ala-NH$_2$ and Y is a member selected from the group consisting of isobutyl and benzyl.

4. The compound of claim 1 wherein said pharmaceutically acceptable addition salt is a member selected from the group consisting of the hydrochloride, hydrobromide, hydroiodide, sulfate, phosphate, acetete, propionate, lactate, meleate, malate, succinate and tartrate.

5. The compound of claim 4 wherein said addition salt is acetate.

6. The compound of claim 4 wherein said addition salt is sulfate.

7. A pharmaceutical composition comprising:

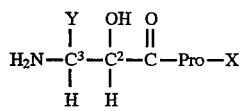

or a pharmaceutically acceptable addition salt thereof, wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid having a radius of gyration of less than 1.54 Å, X also having a carboxyl or a carboxyamide moiety at its carboxy terminus.

8. The pharmaceutical composition of claim 7 wherein X has 2 amino acid residues.

9. The pharmaceutical composition of claim 8 wherein X is -Pro-Ala-HN$_2$.

10. The pharmaceutical composition of claim 9 wherein said pharmaceutically acceptable addition salt is a member selected from the group consisting of the hydrochloride, hydrobromide, hydroiodide, sulfate, phosphate, acetate, propionate, lactate, maleate, realate, succinate, and tartrate.

11. The pharmaceutical composition of claim 10 in unit dosage form.

12. The pharmaceutical composition of claim 11 wherein said pharmaceutically acceptable carrier is a pharmaceutically acceptable fluid suitable for intravenous infusion.

13. The pharmaceutical composition of claim 10 wherein said pharmaceutically acceptable addition salt is sulfate.

14. The pharmaceutical composition of claim 10 wherein said pharmaceutically acceptable addition salt is acetate.

15. The pharmaceutical composition of claim 10 wherein Y is isobutyl.

16. The pharmaceutical composition of claim 10 wherein Y is benzyl.

17. A method of inhibiting bradykinin degradation in a mammalian patient comprising:

administering to a mammalian patient in need of inhibition of bradykinin degradation, a therapeutically effective amount of a compound of the formula:

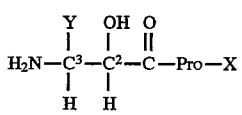

or a pharmaceutically acceptable addition salt thereof, wherein $C^3$ and $C^2$ in combination have the configuration S,R or R,S;

wherein Y is straight or branched chain lower alkyl having 1 to 6 carbon atoms, straight or branched chain lower alkenyl or alkynyl having 2–6 carbon atoms, cyclic alkyl or alkenyl having 5 or 6 carbon atoms, or benzyl; and wherein X is an amino acid or an oligopeptide having from 1 to 8 amino acid residues, the first amino acid residue at the N-terminus of X being a natural or a synthetic L-amino acid having a radius of gyration of less than 1.54 Å, X also having a carboxyl or a carboxyamide moiety at its carboxy terminus.

18. The method of claim 17 wherein said mammalian patient is a human.

19. The method of claim 18 wherein said oligopeptide has two amino acid residues.

20. The method of claim 19 wherein X is the oligopeptide -Pro-Ala-NH$_2$.

21. The method of claim 18 wherein said pharmaceutically acceptable addition salt comprises a member selected from the group consisting of the hydrochloride, hydrobromide, hydroiodide, sulfate, phosphate, acetate, propionate, lactate, maleate, matate, succinate, and tartrate.

22. The method of claim 21 wherein said pharmaceutically acceptable addition salt is sulfate.

23. The method of claim 21 wherein said pharmaceutically acceptable addition salt is acetate.

24. The method of claim 17 further comprising the step of coadministering a therapeutically effective amount of an inhibitor to angiotensin converting enzyme.

25. The method of claim 24 wherein said compound and said inhibitor of angiotensin converting enzyme are administered to said patient by mouth.

26. The method of claim 24 wherein said compound and said inhibitor of angiotensin converting enzyme are administered parenterally to said patient.

27. The method of claim 24 wherein said inhibitor of angiotensin convening enzyme is a member selected from the group consisting of captopril, enalapril, enalaprilat, lisinopril, quinapril, benazepril, fosinopril, ramipril, and ramiprilat.

28. The method of claim 27 wherein said inhibitor of angiotensin convening enzyme is captopril.

29. The method of claim 27 wherein said inhibitor of angiotensin converting enzyme is enalapril.

30. The method of claim 27 wherein said inhibitor of angiotensin converting enzyme is enalaprilat.

31. The method of claim 27 wherein said inhibitor of angiotensin converting enzyme is lisinopril.

32. The method of claim 23 wherein said inhibitor of angiotensin converting enzyme is a member of the group consisting of ramipril and ramiprilat.

* * * * *

UNITED STATES PATENT AND TRADEMARK OFFICE
CERTIFICATE OF CORRECTION

PATENT NO. : 5,656,603
DATED : August 12, 1997
INVENTOR(S) : Simmons

It is certified that error appears in the above-indentified patent and that said Letters Patent is hereby corrected as shown below:

Column 3, line 34, "[$^3$]H-Bk" should be --[$^3$H]-Bk--

Column 4, line 57, "Gh (1.77)" should be --Glu (1.77)--

Column 5, line 1, "realate," should be --malate,--

Column 6, line 14, "($\beta$M)" should be --($\mu$M)--

Column 8, line 18, "microsoma/" should be --microsomal--

Column 8, line 34, "(dam" should be --(data--

Column 9, line 40, "glueans" should be --glucans--

Column 11, line 29, " mount"" should be --amount"--

Column 11, line 56, "Enalapfil" should be --Enalapril--

Column 11, line 60, "convened" should be --converted--

Column 11, last line, "(2S,3aS,6aS)-I[" should be --(2S,3aS,6aS)-1[--

Column 12, line 3, "aliacid" should be --diacid--

Column 12, line 59, "girl" should be --gift--

Column 12, line 62, "Bachera" should be --Bachem--

UNITED STATES PATENT AND TRADEMARK OFFICE
CERTIFICATE OF CORRECTION

PATENT NO. : 5,656,603
DATED : August 12, 1997
INVENTOR(S) : Simmons

It is certified that error appears in the above-indentified patent and that said Letters Patent is hereby corrected as shown below:

Column 13, line 23, "Lalaninamide" should be --L-alaninamide--

Column 13, line 29, "tripepride" should be --tripeptide--

Column 13, line 29, "benzotfiazole-" should be --benzotriazole--

Column 15, line 4, "$\beta$-Na" should be --$\beta$-NA--

Column 15, line 10, "1-like" should be --l-like--

Column 15, line 10, "CEC 3.4.14:1)" should be --(EC 3.4.14.1)--

Column 15, line 11, "naphthalarnide" should be --naphthalamide--

Column 17, line 4, after "$_{ACE}$]," insert --i.e.,--

Column 17, line 52, "*IntraceHular*" should be --*Intracellular*--

Column 17, line 58, "Waiter" should be --Walter--

UNITED STATES PATENT AND TRADEMARK OFFICE
CERTIFICATE OF CORRECTION

PATENT NO. : 5,656,603
DATED : August 12, 1997
INVENTOR(S) : Simmons

It is certified that error appears in the above-indentified patent and that said Letters Patent is hereby corrected as shown below:

Column 18, line 3, "Orawsld" should be --Orawski--

Column 19, line 31, "realate" should be --malate--

Column 20, line 25, "matate" should be --malate--

Column 20, line 41, "convening" should be --converting--

Column 20, line 46, "convening" should be --converting--

Signed and Sealed this

Eleventh Day of November, 1997

Attest:

BRUCE LEHMAN

Attesting Officer

Commissioner of Patents and Trademarks